US012310852B2

(12) United States Patent
Serraf et al.

(10) Patent No.: US 12,310,852 B2
(45) Date of Patent: May 27, 2025

(54) CHORDA REPLACEMENT APPARATUS AND METHOD

(71) Applicant: TEL HASHOMER MEDICAL RESEARCH, INFRASTRUCTURE AND SERVICES LTD., Ramat Gan (IL)

(72) Inventors: Alain Elie Serraf, Jerusalem (IL); Mila Shai Raziel Tejman-Yarden, Tel Aviv (IL); Roey Shafrir, Maccabim Reut (IL)

(73) Assignee: TEL HASHOMER MEDICAL RESEARCH, INFRASTRUCTURE AND SERVICES LTD., Ramat Gan (IL)

( * ) Notice: Subject to any disclaimer, the term of this patent is extended or adjusted under 35 U.S.C. 154(b) by 653 days.

(21) Appl. No.: 17/624,437

(22) PCT Filed: Jul. 3, 2020

(86) PCT No.: PCT/IL2020/050745
§ 371 (c)(1),
(2) Date: Jan. 3, 2022

(87) PCT Pub. No.: WO2021/001837
PCT Pub. Date: Jan. 7, 2021

(65) Prior Publication Data
US 2022/0362021 A1  Nov. 17, 2022

Related U.S. Application Data

(60) Provisional application No. 62/870,693, filed on Jul. 4, 2019.

(51) Int. Cl.
*A61F 2/24* (2006.01)
*A61B 17/04* (2006.01)

(52) U.S. Cl.
CPC .......... *A61F 2/2466* (2013.01); *A61F 2/2457* (2013.01); *A61B 17/0469* (2013.01)

(58) Field of Classification Search
CPC .. A61F 2/2466; A61F 2/2457; A61F 17/0469; A61B 17/0401;
(Continued)

(56) References Cited

U.S. PATENT DOCUMENTS

2005/0021057 A1* 1/2005 St. Goar ............... A61B 17/122
606/144
2007/0118151 A1* 5/2007 Davidson ........... A61B 17/0469
606/151
(Continued)

FOREIGN PATENT DOCUMENTS

CN 103037778 A 4/2013
WO WO-2007100268 A2 * 9/2007 ......... A61B 17/0401
(Continued)

OTHER PUBLICATIONS

International Search Report dated Dec. 13, 2020 for corresponding International Application No. PCT/IL2020/050745.

*Primary Examiner* — Sarah W Aleman
*Assistant Examiner* — Mikail A Mannan
(74) *Attorney, Agent, or Firm* — Tarolli, Sundheim, Covell & Tummino LLP

(57) ABSTRACT

Apparatus for coupling a prosthetic chorda to an atrioventricular valve leaflet, the apparatus comprising: a neochorda delivery system comprising a steerable and pushable catheter housing a neochorda attached to a neochorda puncture needle, the catheter operable to push the puncture needle to puncture and thread the neochorda through a papillary muscle of a ventricle; a retriever system comprising a catheter housing a grabber operable to capture the neochorda puncture needle after being threaded through the papillary muscle and withdraw the neochorda puncture needle and
(Continued)

neochorda from the ventricle; and a tissue clamping system comprising a catheter housing distal and proximal tissue clamps deployable to clamp a region of an atrioventricular valve between them and hold the region so that it may be punctured by the puncture needle to deliver the neochorda through the leaflet and to the papillary muscle.

16 Claims, 20 Drawing Sheets

(58) Field of Classification Search
CPC .. A61B 2017/00243; A61B 2017/0409; A61B 17/0482; A61B 17/0625
See application file for complete search history.

(56) References Cited

U.S. PATENT DOCUMENTS

| | | |
|---|---|---|
| 2007/0118154 A1 | 5/2007 | Crabtree |
| 2007/0265702 A1 | 11/2007 | Lattouf |
| 2011/0060407 A1 | 3/2011 | Katai et al. |
| 2012/0239081 A1 | 9/2012 | Gartner |
| 2013/0172682 A1 | 7/2013 | Ransden |
| 2016/0324636 A1* | 11/2016 | Rourke ............... A61F 2/2442 |
| 2017/0252032 A1 | 9/2017 | Hiorth et al. |
| 2018/0042743 A1* | 2/2018 | Syed ............... A61M 25/0043 |

FOREIGN PATENT DOCUMENTS

| | | | |
|---|---|---|---|
| WO | 2012040865 A1 | 4/2012 | |
| WO | WO-2012137208 A1 * | 10/2012 | ......... A61B 17/0401 |

* cited by examiner

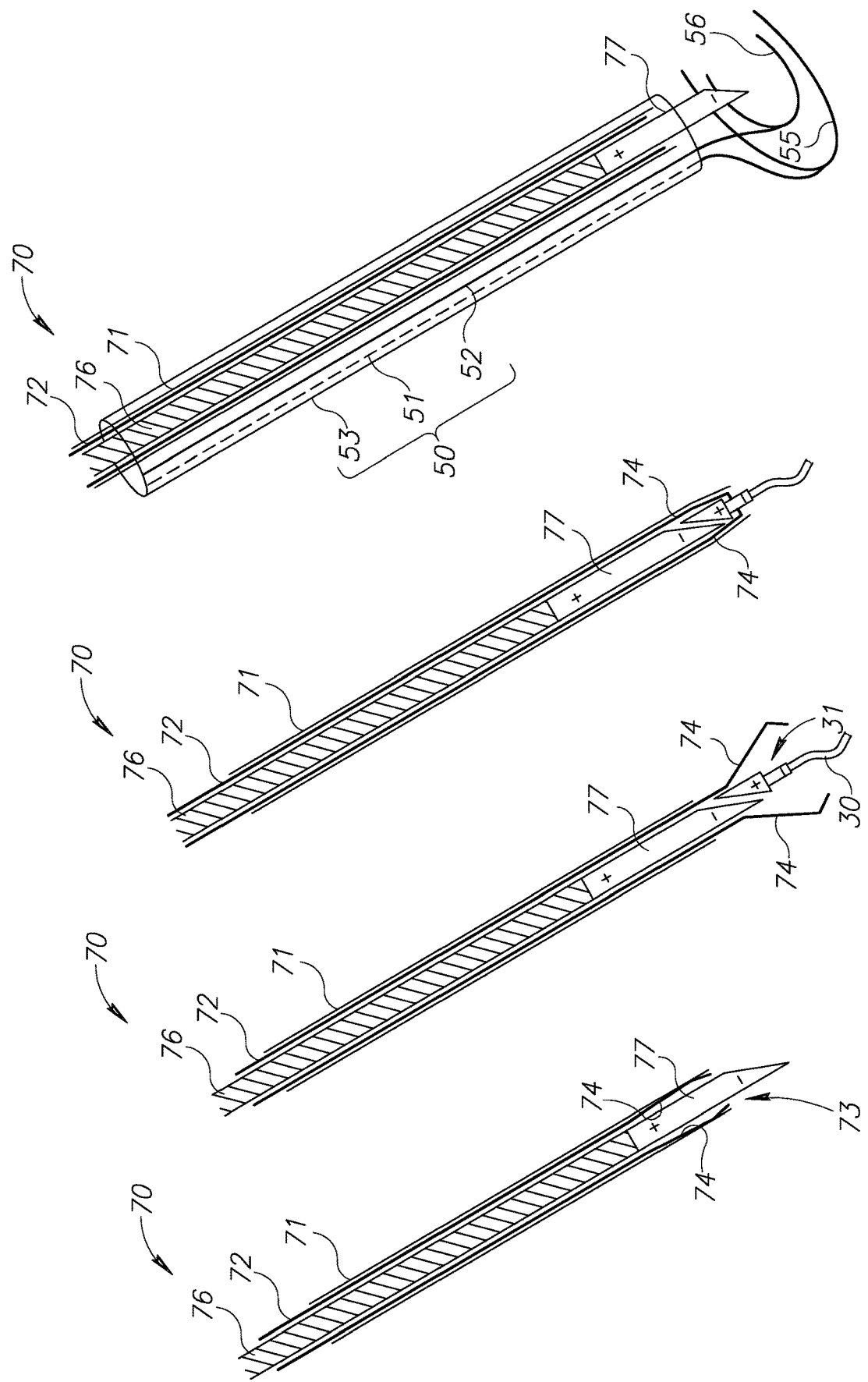

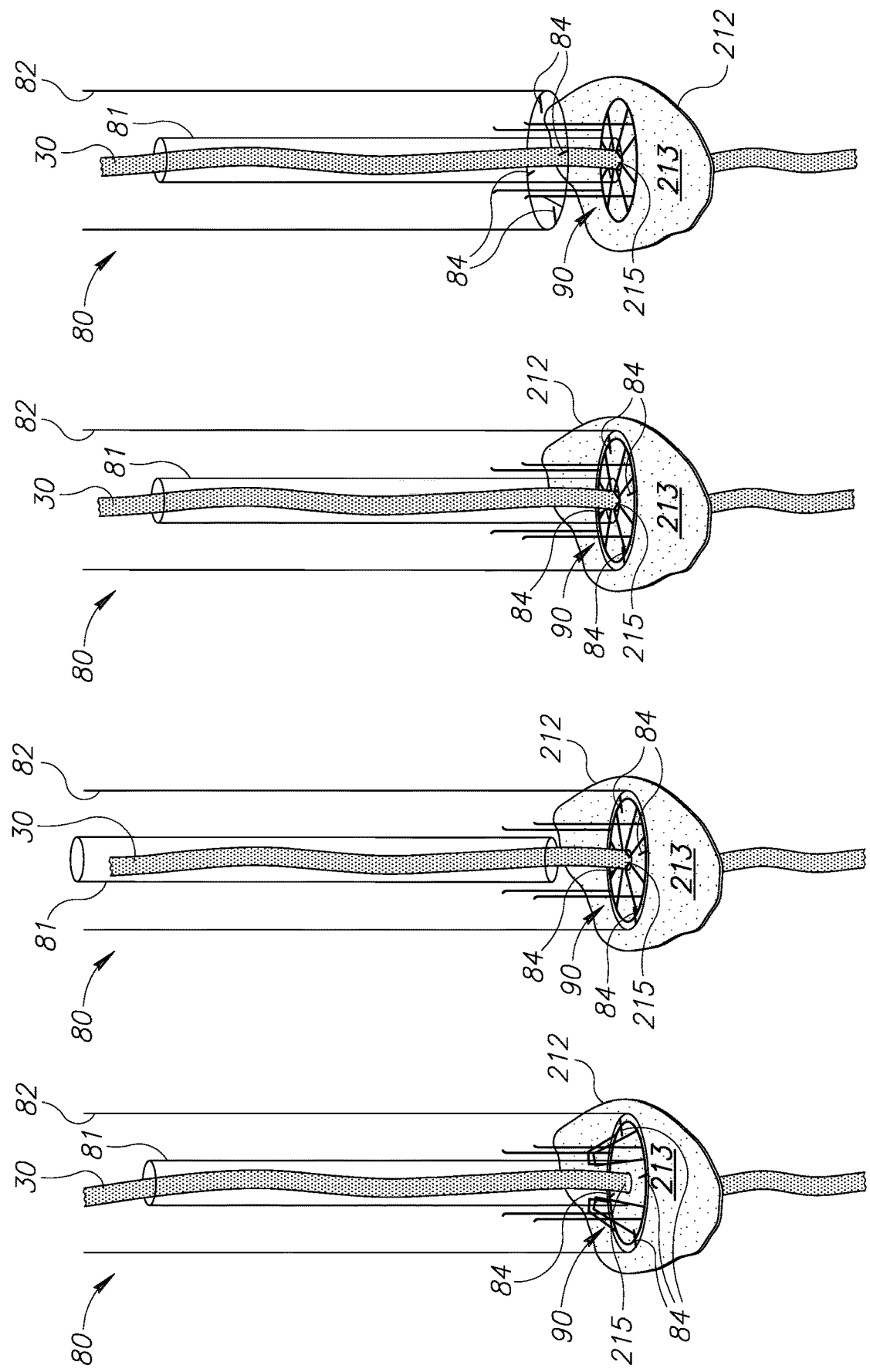

CHORDA REPLACEMENT APPARATUS AND METHOD

RELATED APPLICATIONS

The present application is a U.S. National Stage application under 35 USC 371 of PCT Application Serial No. PCT/IL2020/050745, filed on 3 Jul. 2020, which claims priority from U.S. Provisional Application Ser. No. 62/870,693, filed on 4 Jul. 2019, the entirety of each of which is incorporated herein by reference.

FIELD

Embodiments of the disclosure relate to apparatus and methods for replacing damaged cardiac valve chordae with artificial chordae.

BACKGROUND

The human heart comprises two blood pumps that operate in synchrony to oxygenate and deliver oxygenated blood to the body. A first pump receives deoxygenated blood from the various parts the body and pumps the blood through the lungs to be oxygenated. The second pump receives blood after it has been oxygenated in the lungs and pumps it to flow through the blood vessels of the circulatory system to deliver oxygen and nutrients to the body parts. The two pumps are located adjacent each other in the heart and each pump comprises two chambers, an atrium that receives blood and a ventricle that pumps blood. The first pump is located on the right side of the heart and comprises the right atrium and right ventricle. The second pump is located on the left side of the heart and comprises the left atrium and left ventricle of the heart.

In the first pump, deoxygenated blood enters the right atrium and during a diastolic part of the heart cycle the right ventricle is relaxed and the blood flows from the right atrium through an atrioventricular valve referred to as a tricuspid valve into the right ventricle. The right ventricle contracts during the systolic part of the heart cycle to pump the deoxygenated blood that it receives from the right atrium out of the right ventricle through a pulmonary valve and into the pulmonary artery for delivery to and oxygenation in the lungs. The tricuspid and pulmonary valves control direction of blood flow in the right side of the heart. The tricuspid valve, for example, opens to let deoxygenated blood flow from the right atrium into the right ventricle and closes to prevent deoxygenated blood from regurgitating into the right atrium when the right ventricle contracts.

In the second pump the left atrium receives oxygenated blood from the lungs via pulmonary veins. Oxygenated blood flows from the left atrium into the left ventricle during diastole via a bicuspid atrioventricular valve referred to as the mitral valve. During systole the left ventricle contracts to pump the oxygenated blood that it receives from the left atrium out of the heart through an aortic valve and into the aorta for delivery to the body. The mitral and aortic valves operate to control direction of blood flow in the left side of the heart. For example, the mitral valve opens during diastole to enable blood to flow from the left atrium to the left ventricle and closes to prevent regurgitation of oxygenated blood from the left ventricle to the left atrium during systole when the left ventricle contracts to pump oxygenated blood into the aorta.

Each atrioventricular valve (tricuspid and mitral) that controls blood flow between an atrium and its associated ventricle comprises a set of matching "flaps", also referred to as "leaflets" or "cusps", which are mounted to and extend from a supporting ring structure of fibrous tissue, referred to as the annulus of the valve. The leaflets are passive structures that are operated to open and close the valve by pressure differentials across the valve that contraction and relaxation of the heart muscle generate. The leaflets are configured to align and overlap each other, or coapt, along free edges of the leaflets to close the valve and prevent undesired, retrograde blood flow when blood pressure gradient across the valve increases during cardiac systole. The valve opens and the free edges part when the leaflets are pushed apart from each other by a gradient in blood pressure across the valve that operates to generate antegrade blood flow in a desired, antegrade direction through the valve during cardiac diastole.

Being passive structures, the leaflets of an atrioventricular valve are connected by tendinous cords, referred to as chordae tendineae or simply chordae, to papillary muscles in the ventricle associated with the valve that limit the range of motion of the leaflets during systole to prevent prolapse of the leaflets into the atrium. Damage to the chorda of an atrioventricular leaflet generally results in the leaflet flailing in the cardiac blood stream as the heart pumps and failing to coapt properly with other leaflets, resulting in regurgitation and poor cardiac function. Damage may be so severe as to warrant surgical intervention to effect repair or replacement of the valve and provide a person suffering from cardiac malfunction with an acceptable state of health and quality of life.

SUMMARY

An aspect of an embodiment of the disclosure relates to providing a percutaneous procedure for replacing a damaged chorda of a leaflet in an atrioventricular cardiac valve of a patient's heart with an artificial chorda, and apparatus for performing the procedure. The artificial chorda may be referred to as a "neochorda" and the leaflet having the damaged chorda may be referred to as a "flailing leaflet".

In an embodiment, the procedure comprises percutaneously threading a neochorda delivery system comprising a steerable catheter that encloses a neochorda fiber for replacing the damaged chorda into the ventricle associated with the patient's atrioventricular valve. A distal end of the neochorda may be attached to a needle optionally referred to as a neochorda puncture needle, which is configured for puncturing papillary muscle tissue. Following introduction into the ventricle, the steerable catheter is manipulated to drive the puncture needle and a portion of the neochorda fiber through a papillary muscle in the ventricle. A retriever system is then subcutaneously introduced into the heart, and optionally through the flailing leaflet, into the ventricle. The retriever system is operated to extract the neochorda puncture needle and a length of the neochorda fiber attached to the puncture needle from the ventricle, through the flailing leaflet, and out from the patient's body.

In an embodiment the retriever system comprises a retriever catheter, which encloses a grabber and a pull wire attached to a retriever puncture needle. For introduction through the flailing leaflet, the retriever system may be housed in a tissue clamping system having a clamping catheter that may contain a pair of horseshoe tissue clamps. To introduce the retriever system into the ventricle and extract the chorda puncture needle and neochorda, the clamping catheter comprising the retriever system is threaded into the patient's heart to a retrograde side of the atrioventricular valve. A distal end of the tissue clamping catheter is positioned over the flailing leaflet and the clamps are clamped to a region of the flailing leaflet to stabilize position of the region relative to the clamping catheter distal end. The retriever puncture needle is then driven through the clamped region to carry the grabber into the ventricle, and the grabber is steered to grab and hold the neochorda needle that was driven through the papillary muscle in the ventricle. The pull wire and grabber holding the neochorda needle are then pulled back through the stabilized region of the flailing leaflet into the retriever catheter, and through the tissue clamping catheter to extract the grabber, the neochorda puncture needle that the grabber holds and a length of the neochorda fiber. In an embodiment the retriever puncture needle and/or grabber may comprise a magnetized component to aid in attracting and grabbing the neochorda needle.

After extraction, the neochorda fiber is anchored to the flailing leaflet and the papillary muscle. Excess neochorda fiber is severed and removed from the patient body to leave a functioning neochorda between the leaflet and papillary muscle that reduces flailing of the leaflet and enables the leaflet to coapt properly with another leaflet or other leaflets of the atrioventricular valve.

Optionally, the neochorda is anchored to the flailing leaflet using an anchoring device, also referred to as a "spider-lock", which is slipped onto and locked to the neochorda fiber and leaflet on the retrograde side of the flailing leaflet before the neochorda fiber is severed to remove excess fiber. The spider-lock may be slipped onto and locked to the neochorda fiber and flailing leaflet using a spider-lock deployment system, in accordance with an embodiment of the disclosure. Optionally, the spider-lock deployment system comprises an inner sliding catheter and an outer holding catheter. The catheters hold the spider-lock open and unlocked, and the neochorda fiber slidably inside the inner "sliding" catheter during delivery of the spider-lock to a leaflet anchor position along the neochorda fiber. The spider-lock is closed and locked at the leaflet anchor position by first retracting the inner sliding catheter to lock the spider-lock to the neochorda fiber and then retracting the outer "holding" catheter to lock the spider-lock to the flailing leaflet.

In an embodiment, the neochorda fiber is anchored to the papillary muscle by a knot, which may be referred to as an "anchor", or a crimp-on lock, pre-positioned along the length of the neochorda.

This summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

FIGS. 4A-4C schematically show a retriever system and use of the retriever system to grab and hold the neochorda puncture needle shown in FIGS. 2A-3B, in accordance with an embodiment of the disclosure;

FIG. 4D schematically shows the retriever shown in FIGS. 4A-4C housed in a steerable catheter together with tissue horseshoe clamps to enable an option of driving the retriever through a cardiac leaflet, in accordance with an embodiment of the disclosure;

FIGS. 5A-5H shows details of components of a spider-lock deployment system and illustrate use of the deployment system in accordance with an embodiment;

DETAILED DESCRIPTION

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which the embodiment is intended. Wherever a general term in the disclosure is illustrated by reference to an example instance or a list of example instances, the instance or instances referred to, are by way of non-limiting example instances of the general term, and the general term is not intended to be limited to the specific example instance or instances referred to. Unless otherwise indicated, the word "or" in the description and claims is considered to be the inclusive "or" rather than the exclusive or, and indicates at least one of, or any combination of more than one of items it conjoins.

Figure 1A:
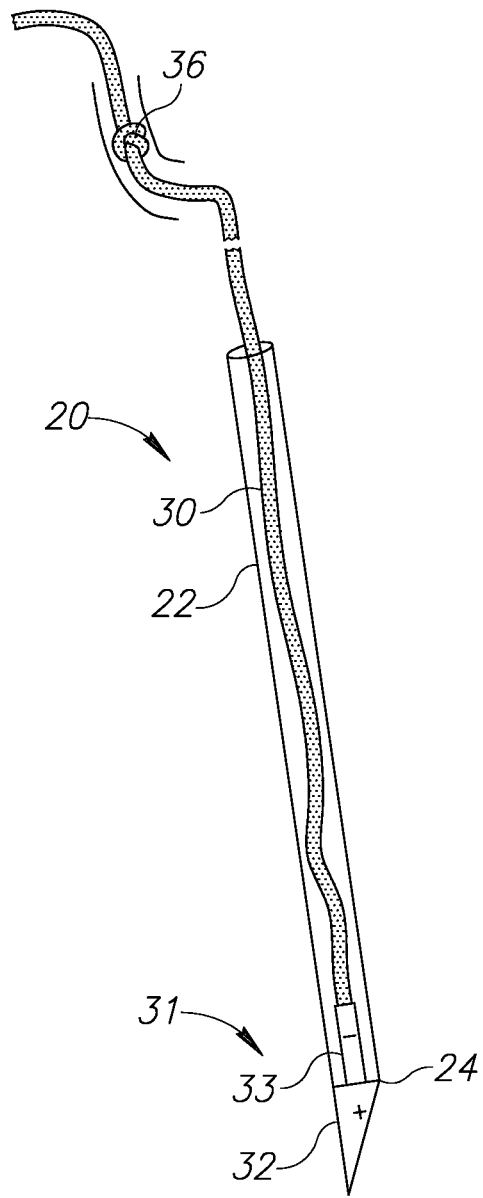
FIGS. 1A and 1B schematically show a neochorda delivery system comprising a steerable catheter housing a length of neochorda fiber attached to an optionally magnetized neochorda puncture needle and respectively having an anchor knot and crimp-on lock, in accordance with an embodiment of the disclosure.

FIG. 1A schematically shows a neochorda delivery system 20 comprising a steerable catheter 22 housing a length of neochorda fiber 30 attached to a neochorda puncture needle 31. In an embodiment the puncture needle comprises a needle head 32 that seats on a distal end 24 of steerable catheter 22 and a stem 33 that seats in the catheter. Needle head 32 remains held to and seated on distal end 24 by maintaining suitable tension on neochorda fiber 30 and optionally by friction between stem 33 and catheter 22. Optionally, puncture needle 31 is magnetized having north and south poles indicated in FIG. 1A by plus and minus signs respectively. Neochorda fiber 30 is optionally tied with an anchor knot 36 for anchoring the neochorda fiber to a papillary muscle or atrioventricular valve leaflet.

Figure 1B:
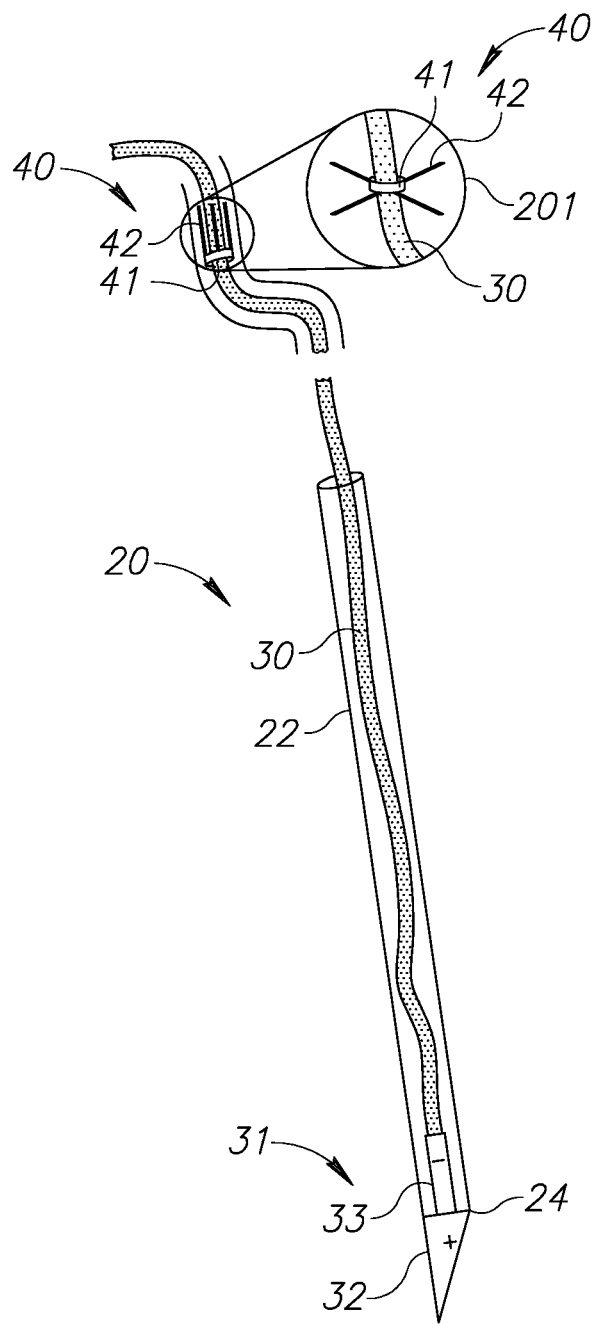

FIG. 1B schematically shows the neochorda delivery system 20 shown in FIG. 1A but having a crimp-on lock 40 instead of a knot for anchoring the neochorda, in accordance with an embodiment of the disclosure. Crimp-on lock 40 is formed from a shape memory material and comprises a ring 41 crimped onto neochorda fiber 30 at a suitable location along the fiber, and a set of legs 42. When inside catheter 22 as shown in FIG. 1B the crimp-on lock is in a folded state with legs 41 folded back in catheter 22 along neochorda fiber 30. When released from catheter 30 the crimp-on lock assumes an expanded state, in which state legs 42 splay out to hook into and anchor the spider-lock to a region of tissue to which it is deployed. Inset 201 in FIG. 1B shows crimp-on lock 40 in an expanded state. Operation of neochorda delivery system 20 is described and discussed below.

Figure 2A:
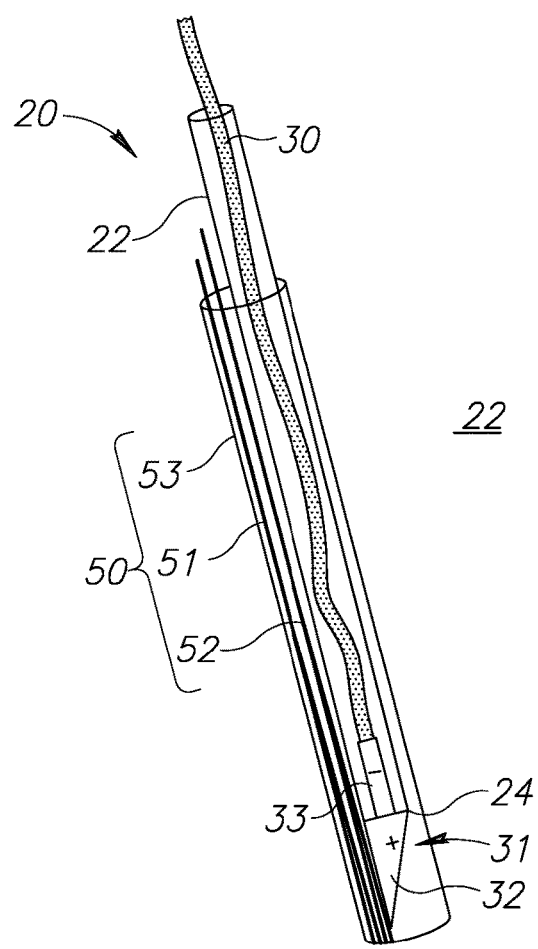
FIG. 2A schematically shows the neochorda delivery system shown in FIG. 1A housed in a steerable catheter together with tissue horseshoe clamps to enable an option of driving the neochorda puncture needle through a cardiac leaflet, in accordance with an embodiment of the disclosure.
Figure 2B:
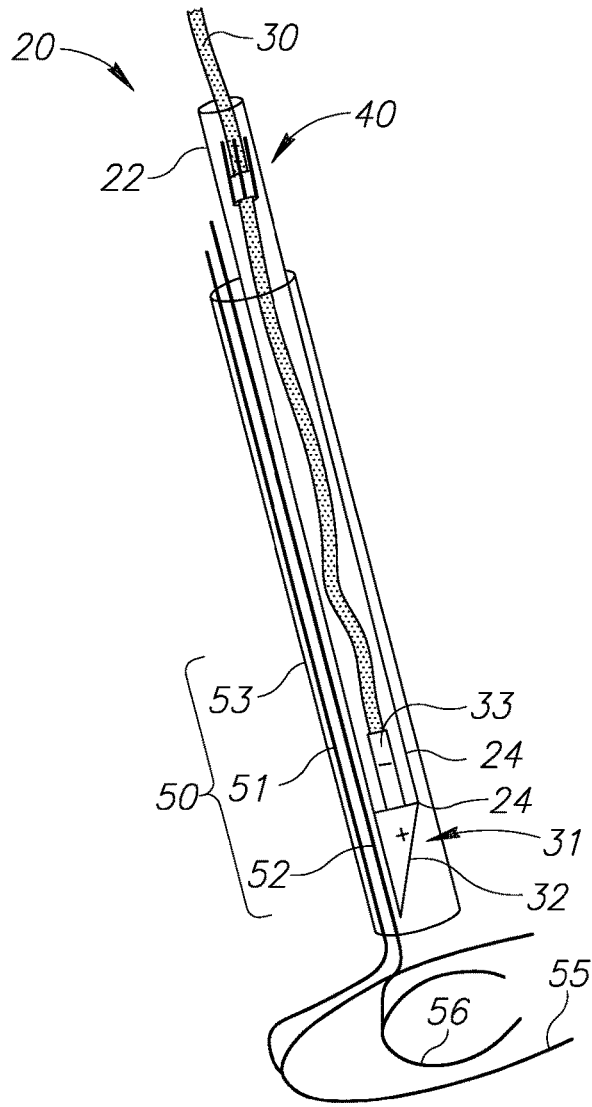
FIG. 2B schematically shows the tissue horseshoe clamps pushed out from the distal end of the catheter shown in FIG. 2A, in accordance with an embodiment of the disclosure.

FIG. 2A schematically shows neochorda delivery system 20 housed in a tissue clamping system 50, that may be used to facilitate operating the neochorda delivery system to puncture a tissue, such as a leaflet of an atrioventricular valve, in accordance with an embodiment of the disclosure. Tissue clamping system 50 optionally comprises distal and proximal tissue horseshoe clamps 51 and 52 housed in a catheter 53. Distal and proximal horseshoe clamps 51 and 52 may be formed from a shape memory material and are held in respective collapsed states inside catheter 53. The horseshoe clamps are configured to assume expanded states in which they are morphed to remembered wireforms ending in horseshoe shapes 55 and 56 respectively when pushed out from catheter 53. The horseshoe shapes are configured to grasp and hold a layer of tissue, such as a cardiac valve leaflet between them. FIG. 2B schematically shows the distal and proximal horseshoe clamps 51 and 52 pushed out from clamping system catheter 53 to assume their respective expanded wireform shapes having horseshoe shape end 55 and 56. It is noted that whereas in FIG. 2B tissue clamps 51 and 52 assume a horseshoe shape when extended out from catheter 53 tissue clamps in accordance with an embodiment may assume shapes other than horseshoe, and may for example assume a sewing machine footer shape, or a simple band shape.

Figures 3A, 3B:
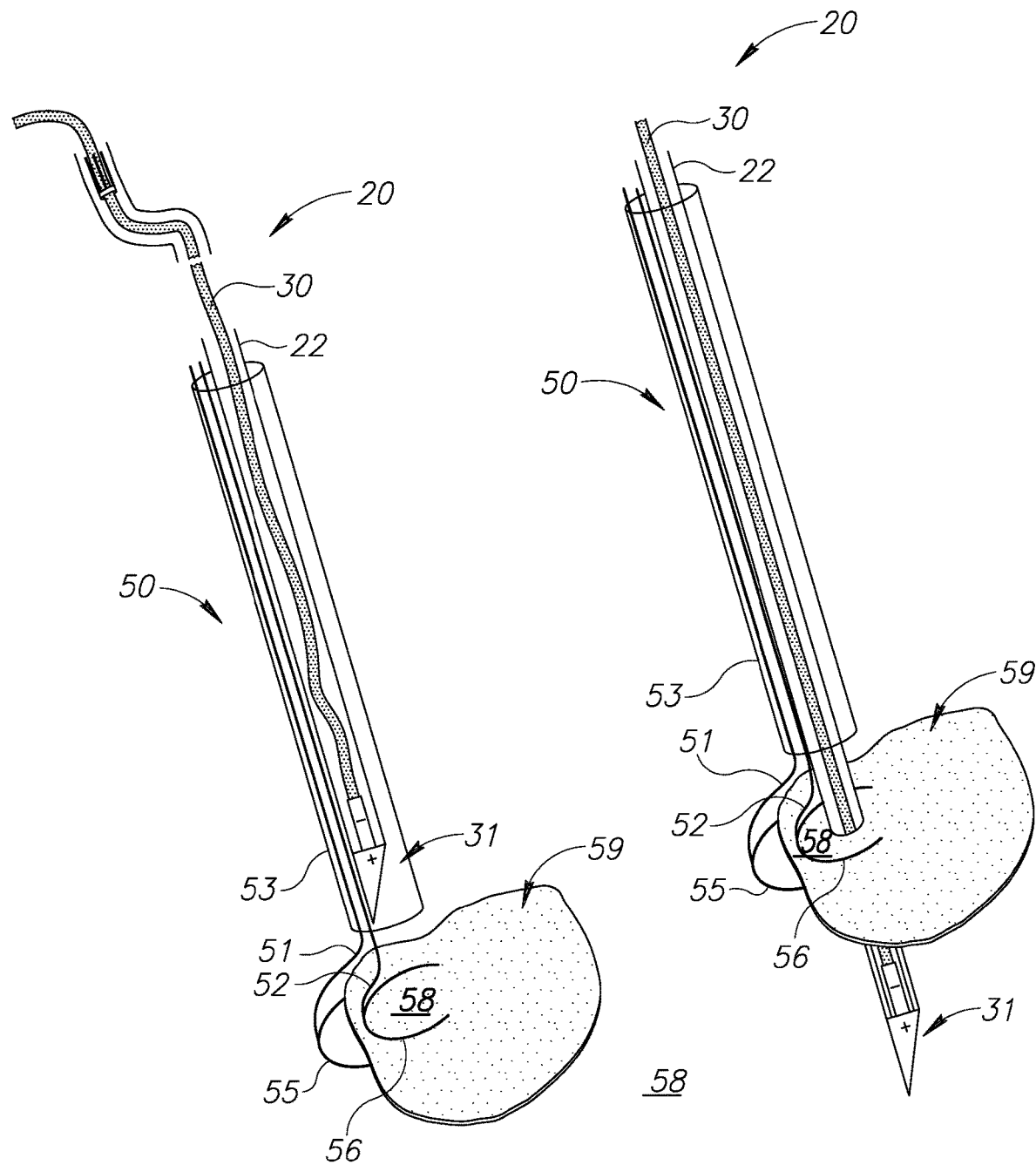
FIGS. 3A and 3B schematically illustrate operating the catheter and tissue horseshoe clamps shown in FIGS. 2A and 2B being used to puncture and drive the neochorda puncture needle and attached length of neochorda fiber through a thin tissue, in accordance with an embodiment of the disclosure.

FIG. 3A schematically shows neochorda delivery system 20 housed in tissue clamping system 50 and horseshoe clamps 51 and 52 pushed out from catheter 53 to grasp and hold a region 58 of tissue 59 between them, in accordance with an embodiment of the disclosure. FIG. 3B schematically shows neochorda delivery system 20 pushed out from catheter 53 to puncture tissue region 58 held between horseshoe clamps 51 and 52, in accordance with an embodiment of the disclosure.

FIG. 4A schematically shows a retriever system 70 configured to attract, grip, and hold ("capture"), neochorda puncture needle 31 (FIG. 3B), and extract the neochorda puncture needle and a length of neochorda fiber 30 attached to the needle out of a patient's body, in accordance with an embodiment of the disclosure.

Retriever system 70 optionally comprises an outer holding catheter 71 and an inner gripping catheter 72. Inner gripping catheter 72 comprises a grabber 73 having a set of gripping jaws 74 at a distal end of the gripping catheter and houses a pushable pull wire 76 attached to a capture needle 77. Capture needle 77 may be magnetized in a direction to generate a magnetic field that attracts the magnetized neochorda puncture needle 31 to capture needle 77. Gripping jaws 74 are optionally formed from a shape memory material and have a remembered shape in which the jaws are open to receive neochorda puncture needle 31, or may be spring loaded to be open, but are constrained closed by outer holding catheter 71 when inside the holding catheter. Inner gripping catheter 72 may be pushed out from outer holding catheter 71 past capture needle 77 to free gripping jaws 74 from outer holding catheter 71 and allow the gripping jaws to open and receive neochorda puncture needle 31. Pull wire 76 may be used to hold capture needle 77 so that inner gripping catheter 72 can be pushed past the capture needle.

FIG. 4B schematically shows inner gripping catheter 72 pushed out from outer holding catheter 71 and gripping jaws 74 open so that the magnetic field of capture needle 77 attracts neochorda needle 31 to enter gripping jaws 74 and contact and adhere to capture needle 31. Once within gripping jaws 74, as schematically shown in FIG. 4C, outer holding catheter 71 may be pushed distally over inner gripping catheter 72 to close gripping jaws 74 and securely hold neochorda puncture needle 31. The gripping jaws and neochorda puncture needle 31 together with a length of neochorda fiber 30 may be extracted from a patient's body by pulling retriever system 70 out of the body, pulling inner gripping catheter 72 out of outer holding catheter 71, and/or pulling pull wire 76 out of inner gripping catheter 72.

Wire 76 may be used to push capture needle 77 out from gripping and holding catheters 72 and 71 so that retriever 70 may puncture and pass through a tissue, such as an atrioventricular valve leaflet, to position the retriever in a desired location. By way of example, FIG. 4D schematically shows retriever 70 assembled to tissue clamping system 50 (shown in FIGS. 3A and 3B housing neochorda delivery system 20), and wire 76 pushed distally to push capture needle 77 out of the retriever so that the retriever may puncture and be passed through a tissue region (not shown in FIG. 4D) held by horseshoe clamps 51 and 52.

Figure 5A:
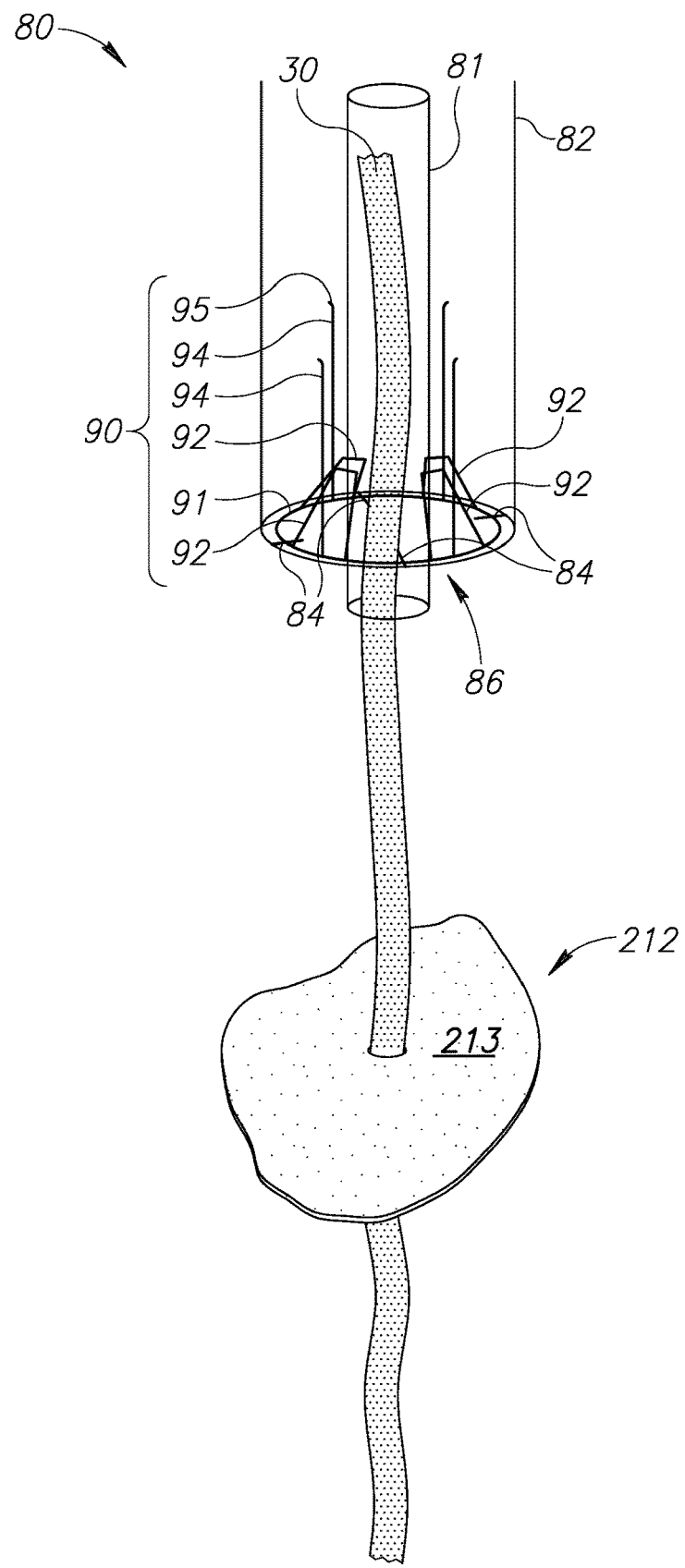

FIG. 5A schematically shows a spider-lock delivery system 80 being slipped over a length of neochorda fiber 30 that has been passed through, by way of example, a region 213 of an atrioventricular valve leaflet 212 to lock a shape memory spider-lock 90 to the neochorda fiber and tissue region, in accordance with an embodiment of the disclosure.

Delivery system 80 comprises an inner slide catheter 81 in which neochorda fiber 30 is free to slide and a concentric outer holding catheter 82. Spider-lock 90 optionally comprises a support ring 91 that supports, optionally four, cable clamps 92 and, optionally four, legs 94 having barbed ends 95. Cable clamps 92 clutch inner slide catheter 81 and barbed ends 95 bite into and hold onto the inside of outer holding catheter 82. Optionally holding catheter 82 comprises engaging prongs 84 that engage support ring 91 to aid in maintaining spider-lock 90 in position at a distal end 86 of holding catheter 82.

Figure 5H:
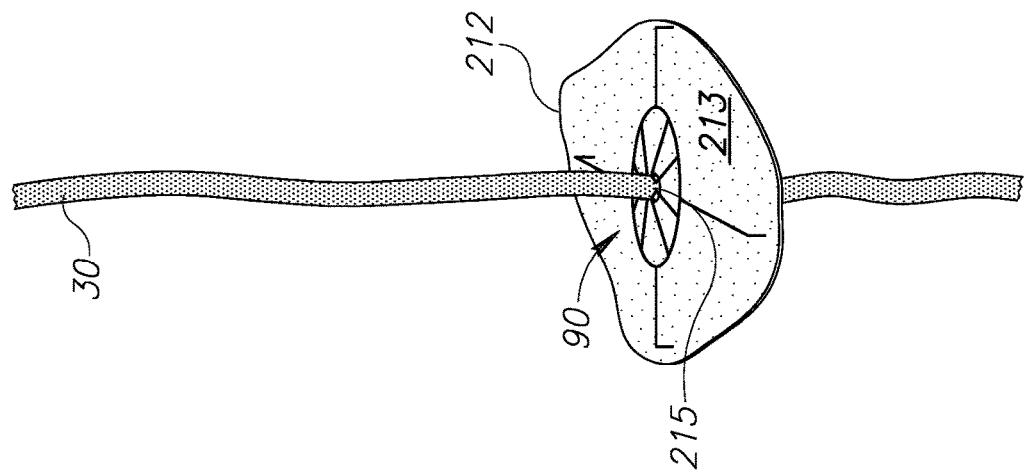
Figure 5G:
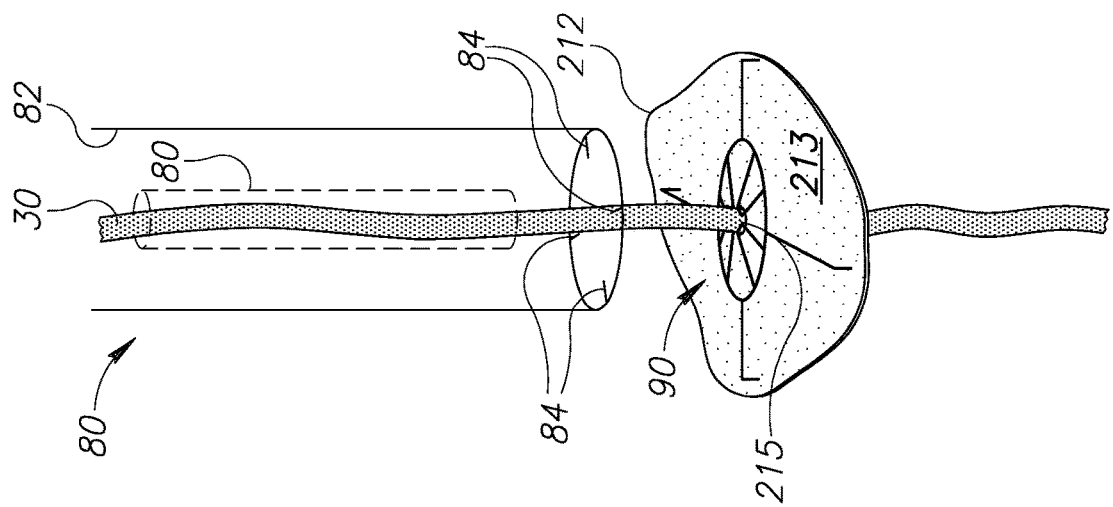
Figure 5F:
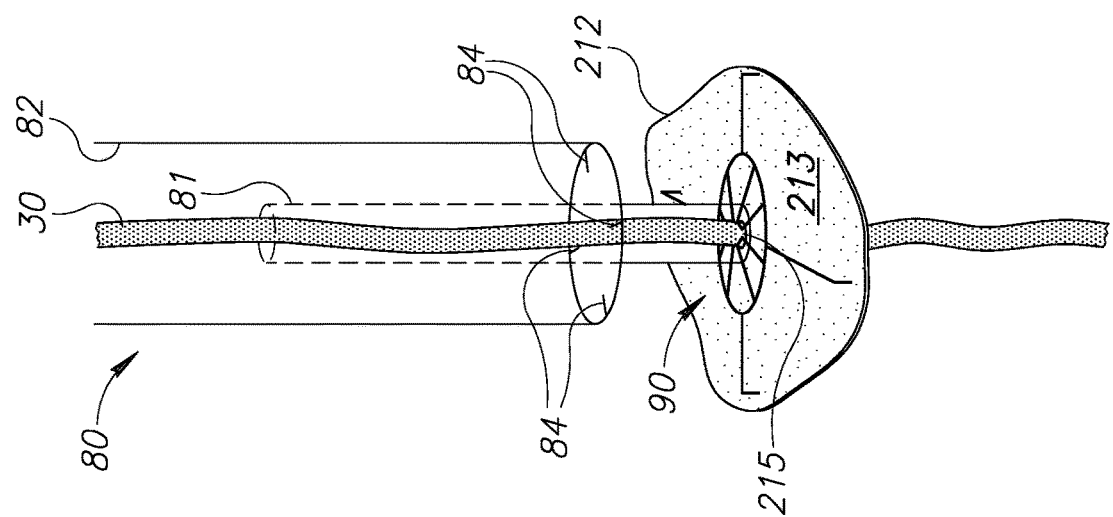

FIG. 5B schematically shows delivery system 80 after the delivery system has been slipped distally over neochorda fiber 30 to an anchoring region 215 along the neochorda fiber suitable for anchoring spider-lock 90 to the neochorda fiber and region 213 of leaflet 212. In FIG. 5C slide catheter 81 is displaced proximally away from spider-lock 90 and anchoring region 213 to enable cable clamps 92 to snap to neochorda fiber 30 and clamp spider-lock 90 to the neochorda fiber. Slide catheter 81 is then displaced distally to contact and seat on cable clamps 92 as shown in FIG. 5D to hold spider-lock in place on leaflet 212 as outer holding catheter is displaced to release spider legs 94 to unfold and attach spider-lock 90 to leaflet 212 as shown in FIGS. 5E and 5F. Thereafter, as schematically shown in FIG. 5G both sliding catheter 81 and holding catheter 82 are removed distally from spider-lock 90 and the patient's body to leave neochorda fiber 30 tied to leaflet 212 as schematically shown in FIG. 5H ready to be severed from excess fiber and leave a prosthetic neochorda in place.

FIGS. 6A-6L schematically illustrate a percutaneous procedure for replacing a chorda of optionally a patient's (not shown) mitral valve anterior leaflet with a neochorda using neochorda delivery system 20, tissue clamping system 50, retriever system 70, and spider-lock delivery system 80, in accordance with an embodiment of the disclosure. The figures schematically show a cutaway of the patient's heart 100 that shows the heart's left atrium 102, left ventricle 104, and mitral valve 110 connecting them. Mitral valve 110 has an annulus 111, anterior leaflet 112, and posterior leaflet 114 shown in FIGS. 6A-6L cutaway to various degrees for convenience of presentation. Optionally, the procedure is carried out under ultrasound transesophageal echocardiography (TTE) and/or ultrasound intra-cardiac echo (ICE) imaging.

Figure 6A:
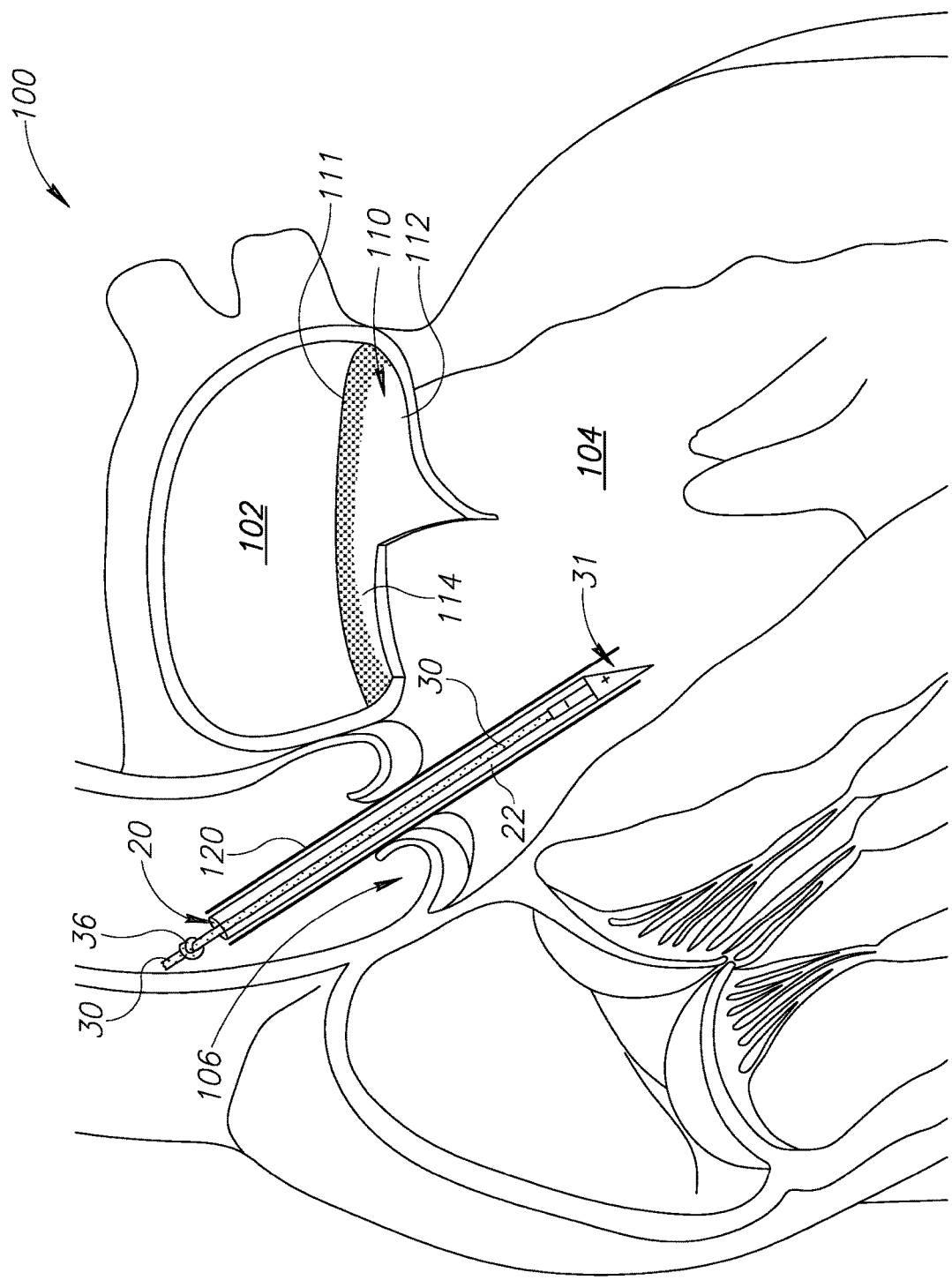
FIGS. 6A-6L schematically illustrate percutaneous deployment of a neochorda to a leaflet of a mitral valve via the aortic valve, in accordance with an embodiment of the disclosure.
Figure 6B:
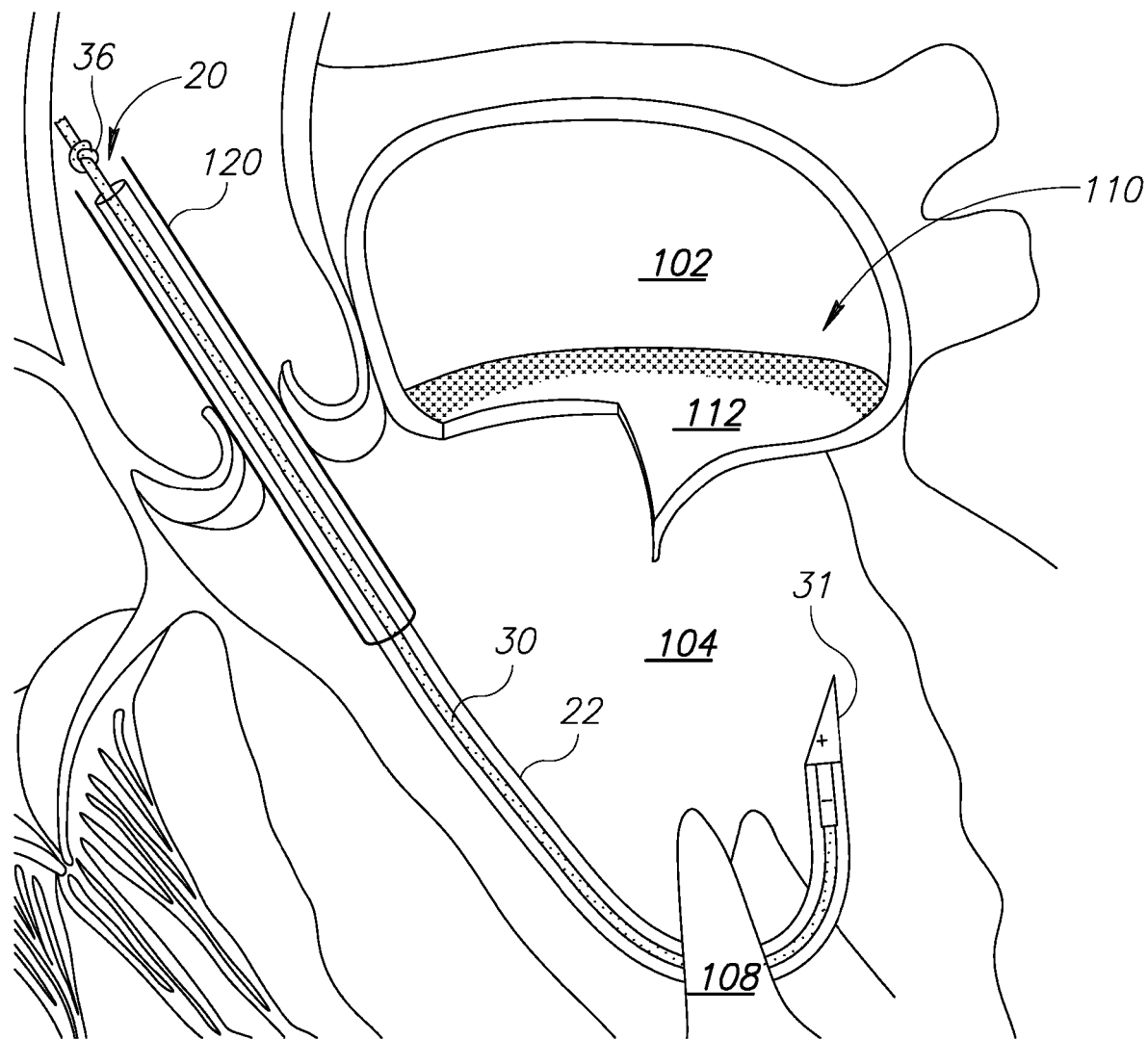
Figure 6C:
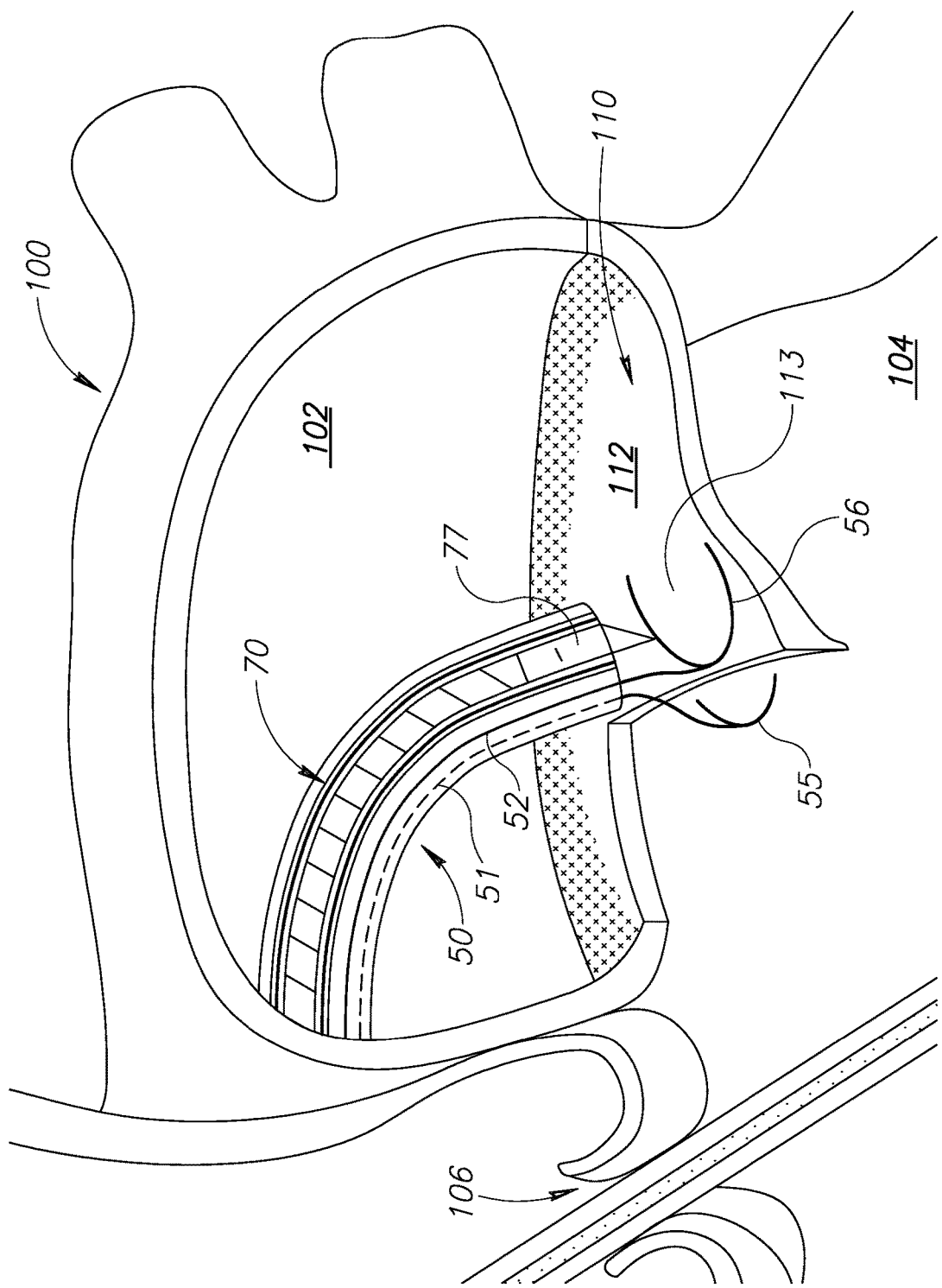

In an embodiment employing a transfemoral approach, a catheter 120 is threaded into the patient's heart 100 and used to introduce neochorda delivery system 20 (FIG. 1A), optionally through the aortic valve 106, and into left ventricle 104 as schematically shown in FIG. 6A. In FIG. 6B catheter 22 of delivery system 20 is pushed out from catheter 120 and steered to push neochorda puncture needle 31 through a papillary muscle 108 in the left ventricle. Thereafter, in a transseptal approach retriever system 70 housed in tissue clamping system 50 (FIG. 4D) is introduced into the left atrium 104 of the heart and horseshoe clamps 51 and 52 deployed to grasp and hold anterior leaflet 112 of mitral valve 110 as schematically shown in FIG. 6C.

Figure 6D:
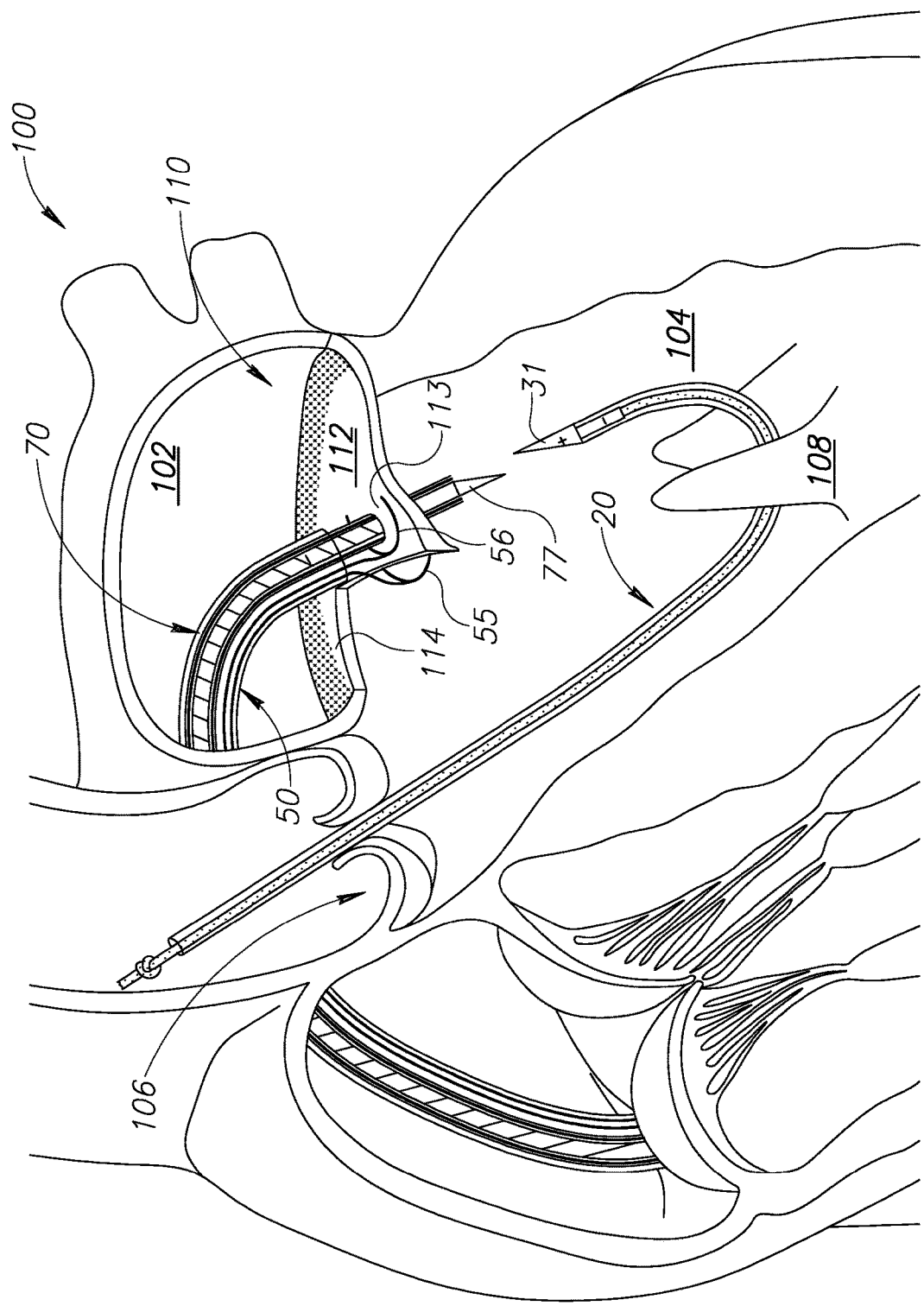

In deploying horseshoe clamps 51 and 52, distal horseshoe clamp 51 is first passed through the opening of mitral valve 110 between edges of the mitral leaflets 112 and 114 along which the leaflets meet and horseshoe end 55 positioned under anterior leaflet 112. Proximal horseshoe clamp 52 is then extended to and horseshoe end 56 positioned over anterior leaflet 112. The distal and proximal horseshoe clamps are then maneuvered to close to each other and clamp a desired region of the anterior leaflet between them. FIG. 6C schematically shows distal and proximal clamps 51 and 52 deployed and horseshoes 55 and 56 clamping a desired region 113 of anterior leaflet 112 between them. Retriever 70 is then pushed out of tissue clamping system 50 to puncture through anterior leaflet 112 in region 113 clamped by clamping system 50 and enter ventricle 104. FIG. 6D schematically shows retriever 70 after the retriever has entered the ventricle.

Figure 6E:
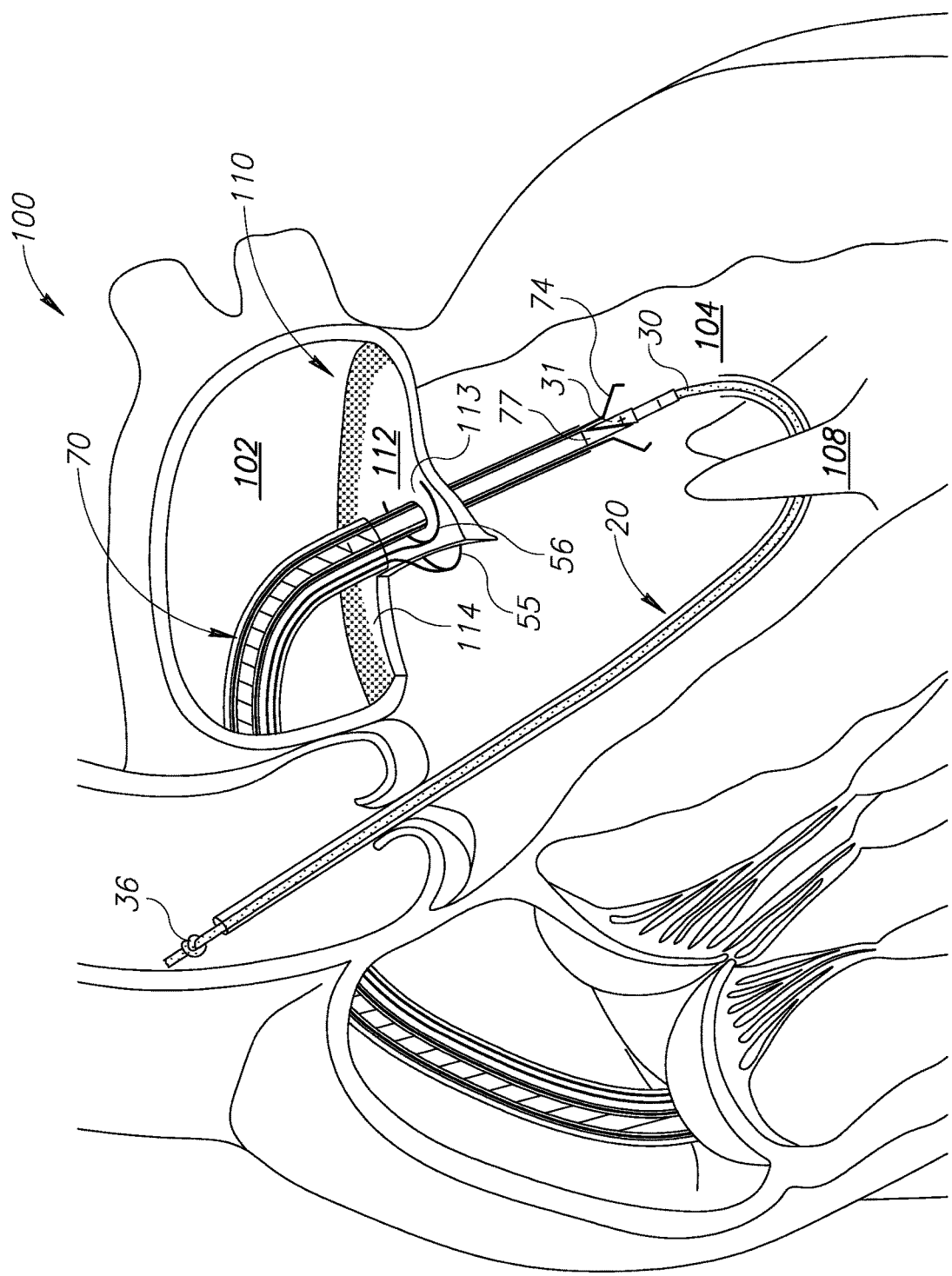
Figure 6F:
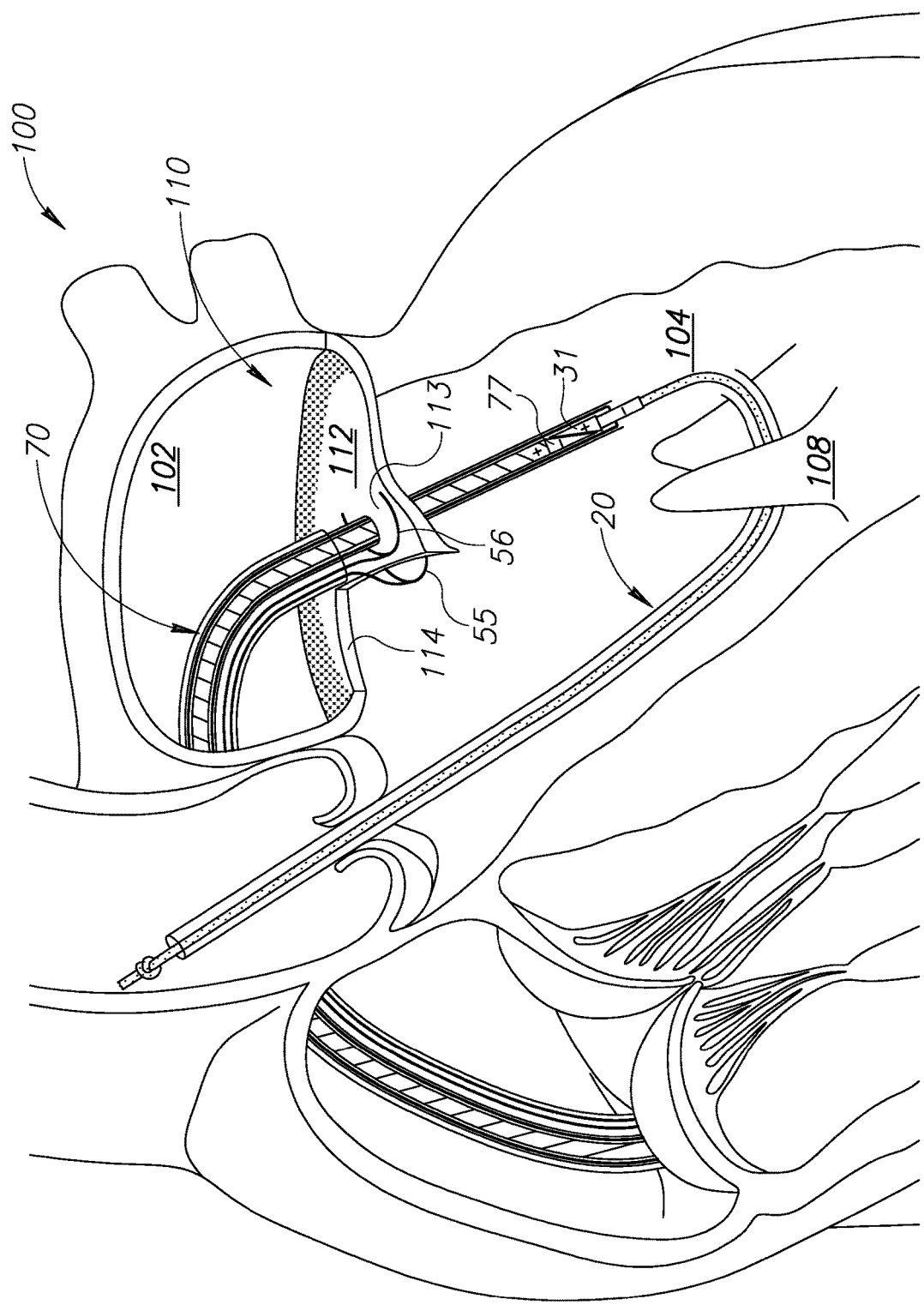
Figure 6G:
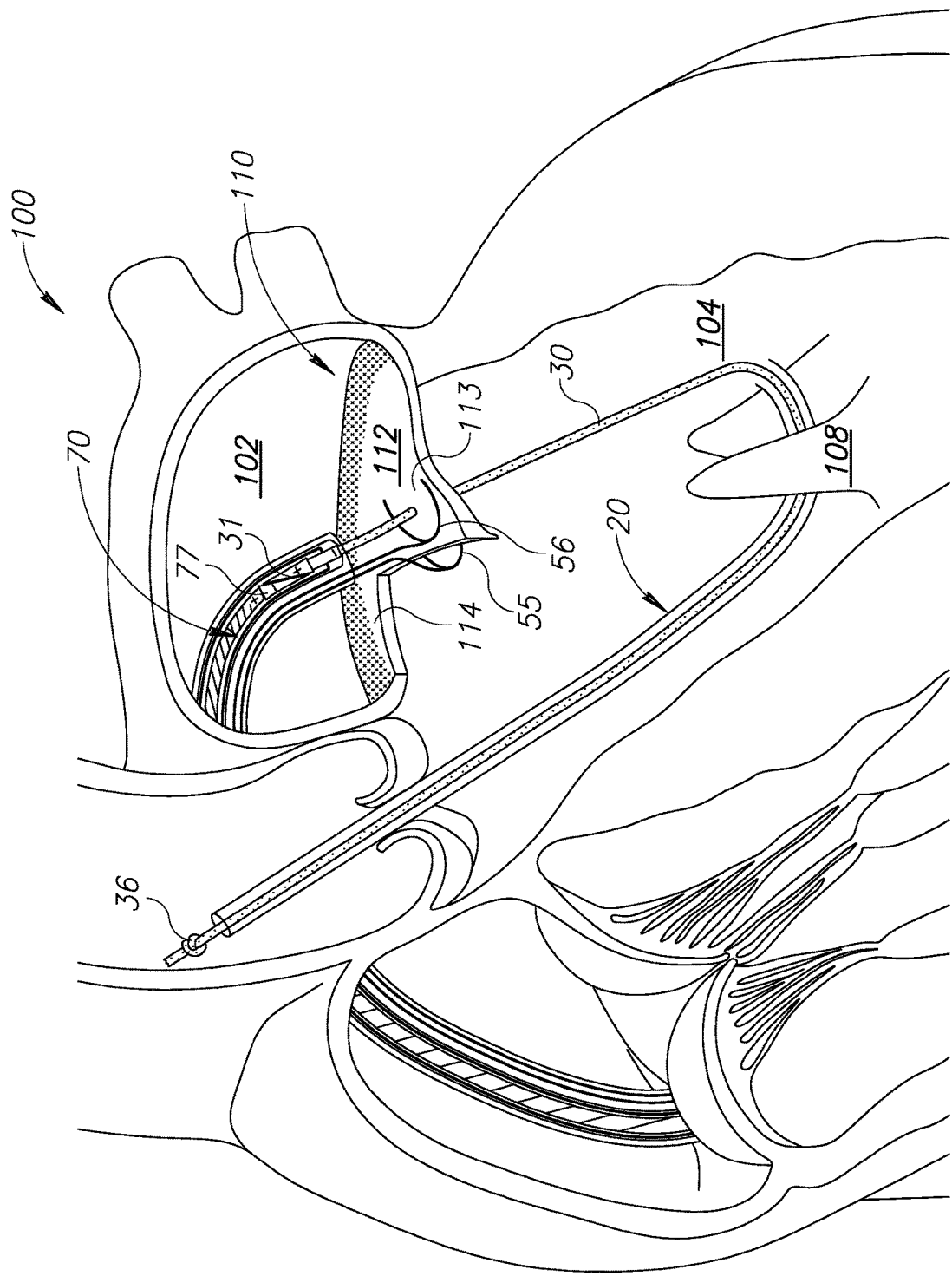
Figure 6H:
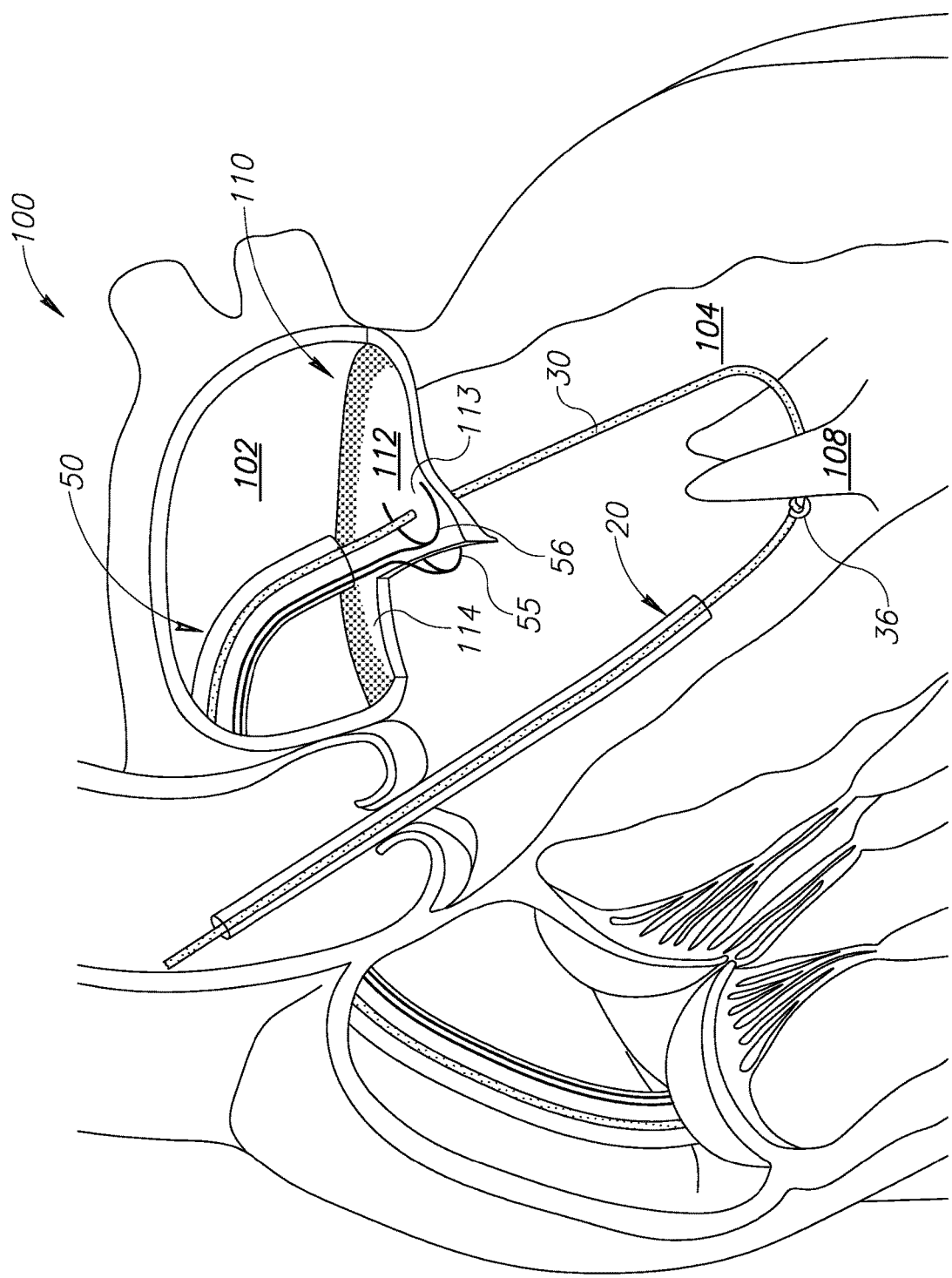
Figure 6I:
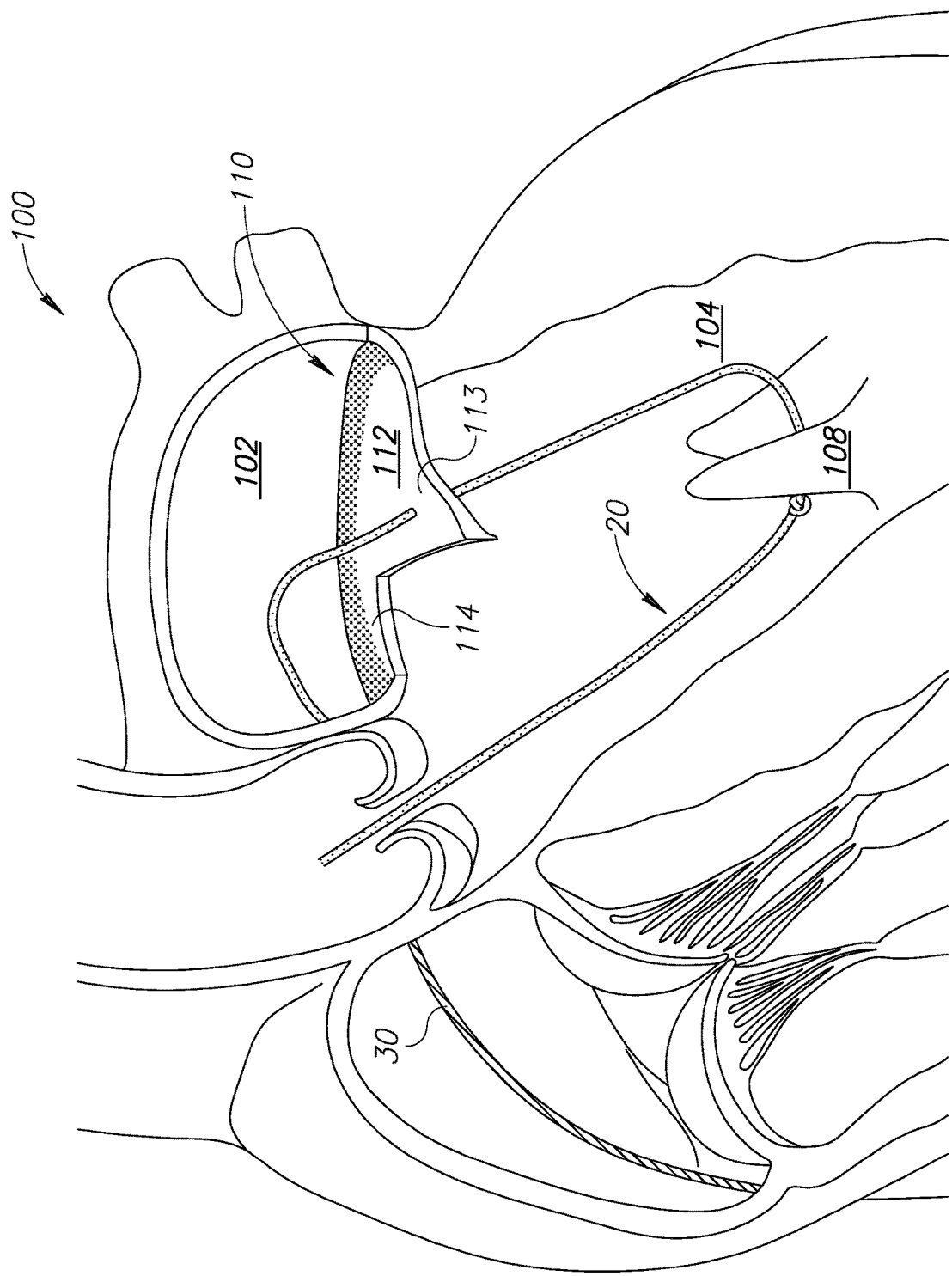

After being introduced into ventricle 104 retriever 70 is operated to capture neochorda needle 31 as described above with reference to FIGS. 4A-4C. FIGS. 6E and 6F schematically illustrate retriever system 70 capturing neochorda needle 31 in ventricle 104 of heart 100. Retriever system 70 is then withdrawn from ventricle 104 through region 113 clamped by horseshoe clamps 51 and 52 to draw neochorda needle 31 and a length of neochorda fiber 30 into tissue clamping system catheter 53 and out from heart 100 to outside of the patient's body. Neochorda needle 31 and neochorda fiber 30 are drawn to a distance outside the patient's body so that anchor knot 36 tied in the neochorda fiber is lodged and anchors the neochorda fiber in papillary muscle 108. FIG. 6H schematically shows neochorda fiber 30 in heart 100 and clamping system catheter 53 after anchor knot 36 is lodged in papillary muscle 108. Horseshoe clamps 51 and 52 are then disengaged from anterior leaflet 112, retracted into tissue clamping system catheter 53 and clamping system 50 removed from the body leaving neochorda fiber 30 anchored in papillary muscle and threaded through heart 100 and inferior vena cava (IV) to outside the body. FIG. 6I schematically shows neochorda fiber 30 after clamping system 50 is removed from the patient's body.

Figure 6J:
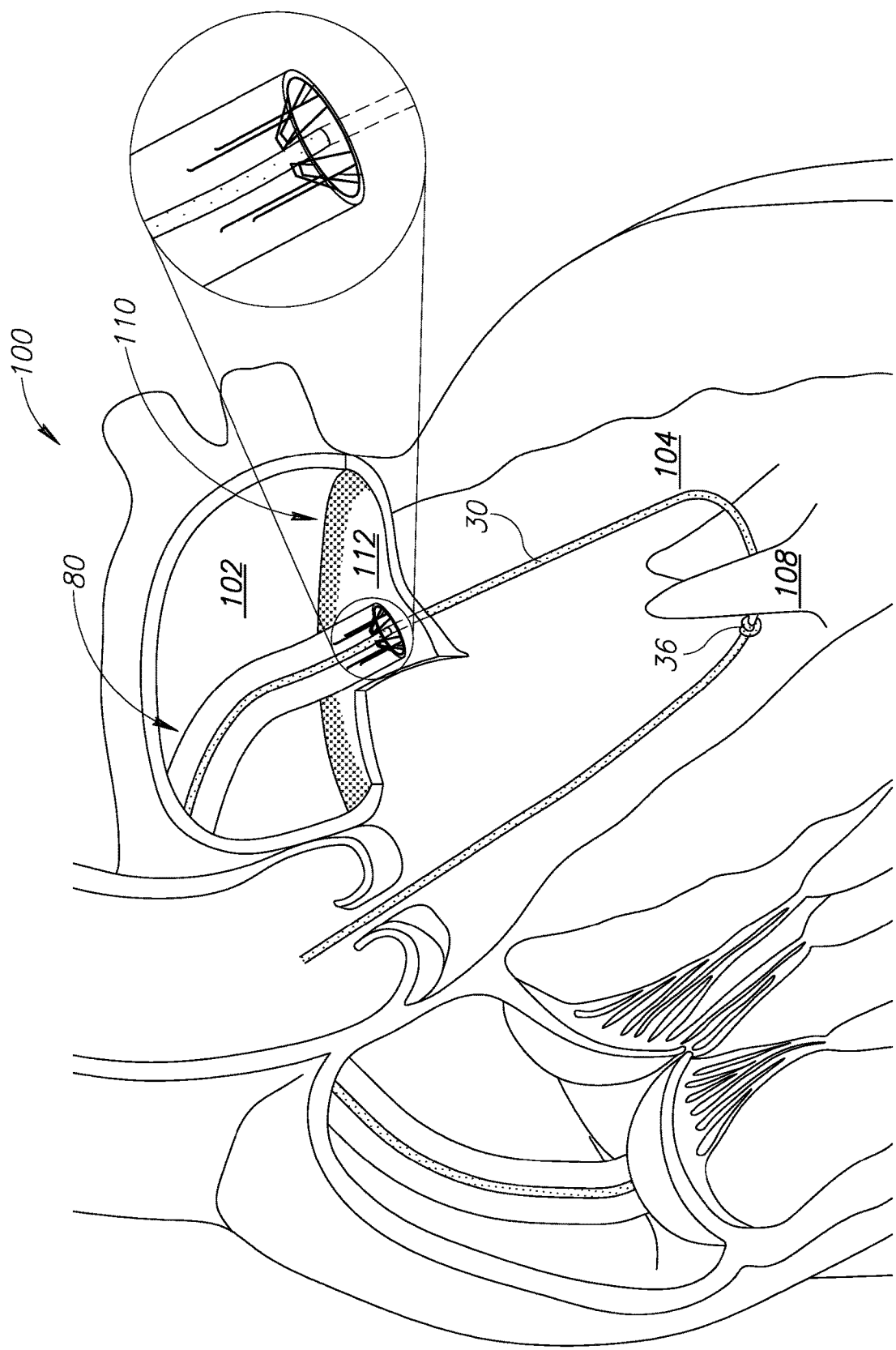
Figure 6K:
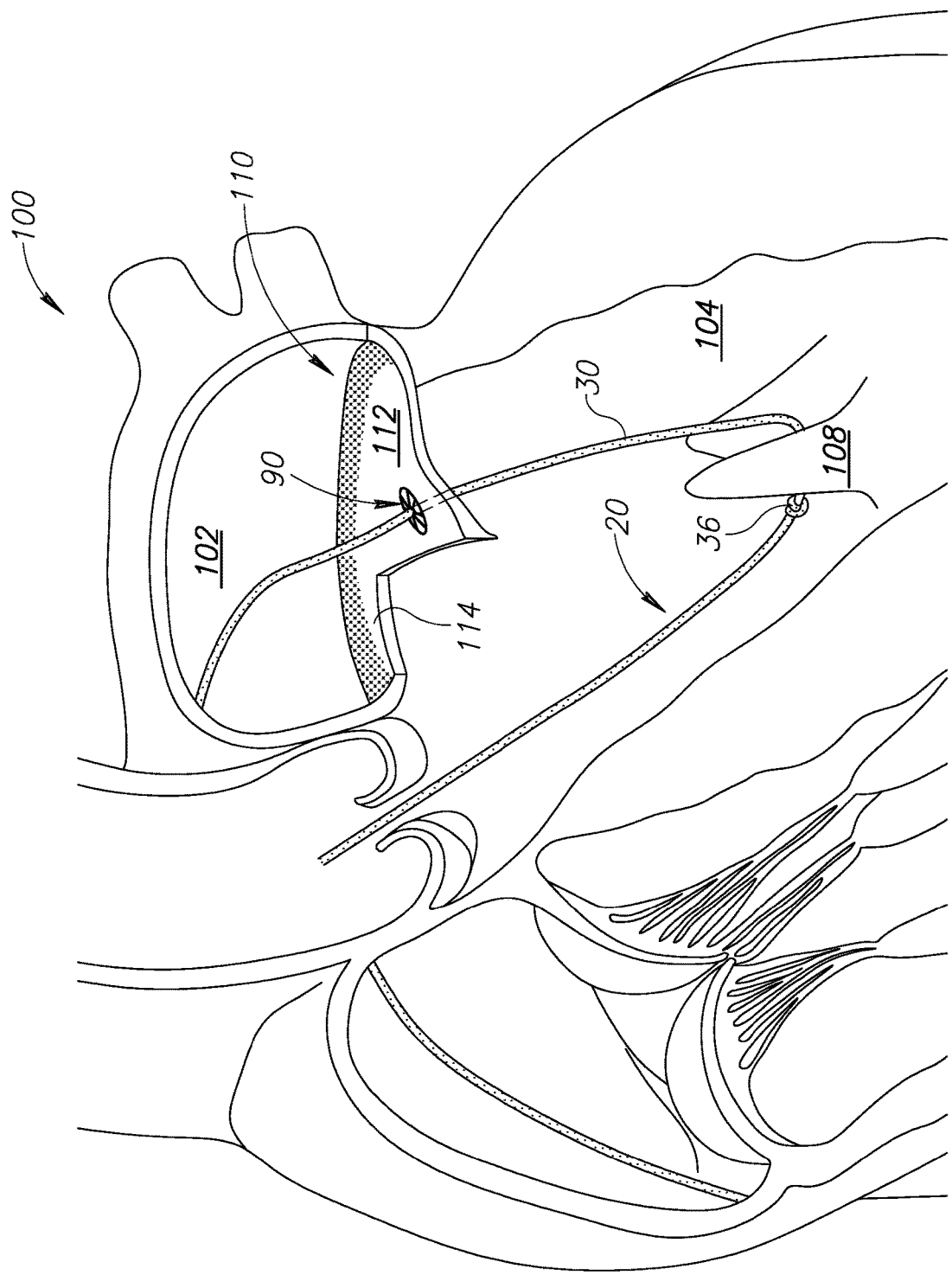
Figure 6L:
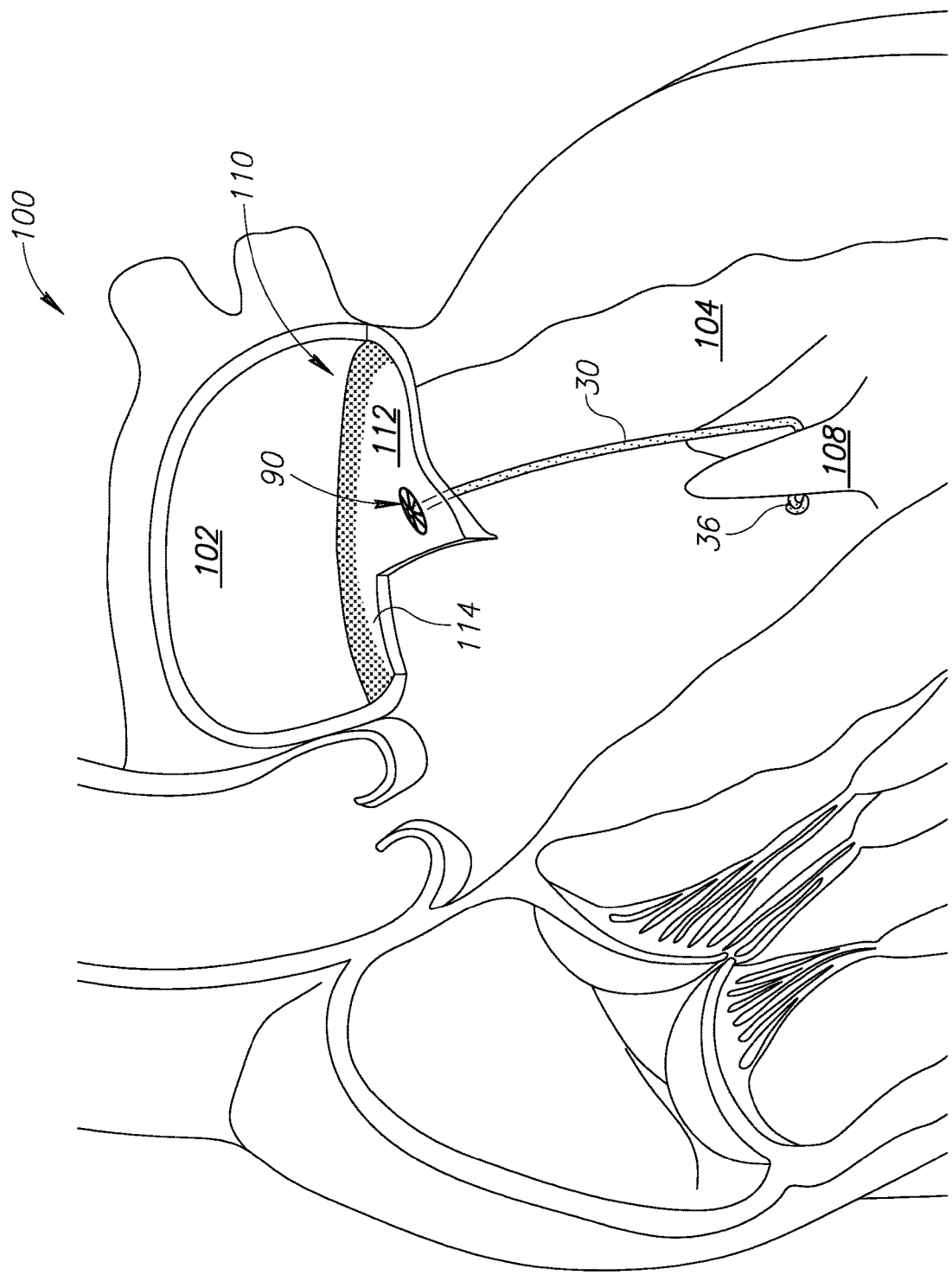

In an embodiment, after removal of clamping system 50 spider-lock delivery system 80 (FIGS. 5A-5H) is threaded over neochorda fiber 30 to enter left atrium 102 and position spider-lock 90 on the retrograde side of anterior leaflet 112 as schematically shown in FIG. 6J. Spider-lock delivery system 80 is then operated as shown in FIGS. 5A-5H to lock spider-lock 90 to neochorda fiber 30 and anterior leaflet 112. The delivery system is then removed from the body leaving neochorda fiber 30 anchored to papillary muscle 108 and anterior leaflet 112, as schematically shown in FIG. 6K. Excess neochorda fiber extending from the papillary muscle through the heart and vena cava to outside the body and from papillary muscle 108 through the aortic valve and femoral artery to outside the body is removed to leave a function neochorda as shown in FIG. 6L.

Figure 7:
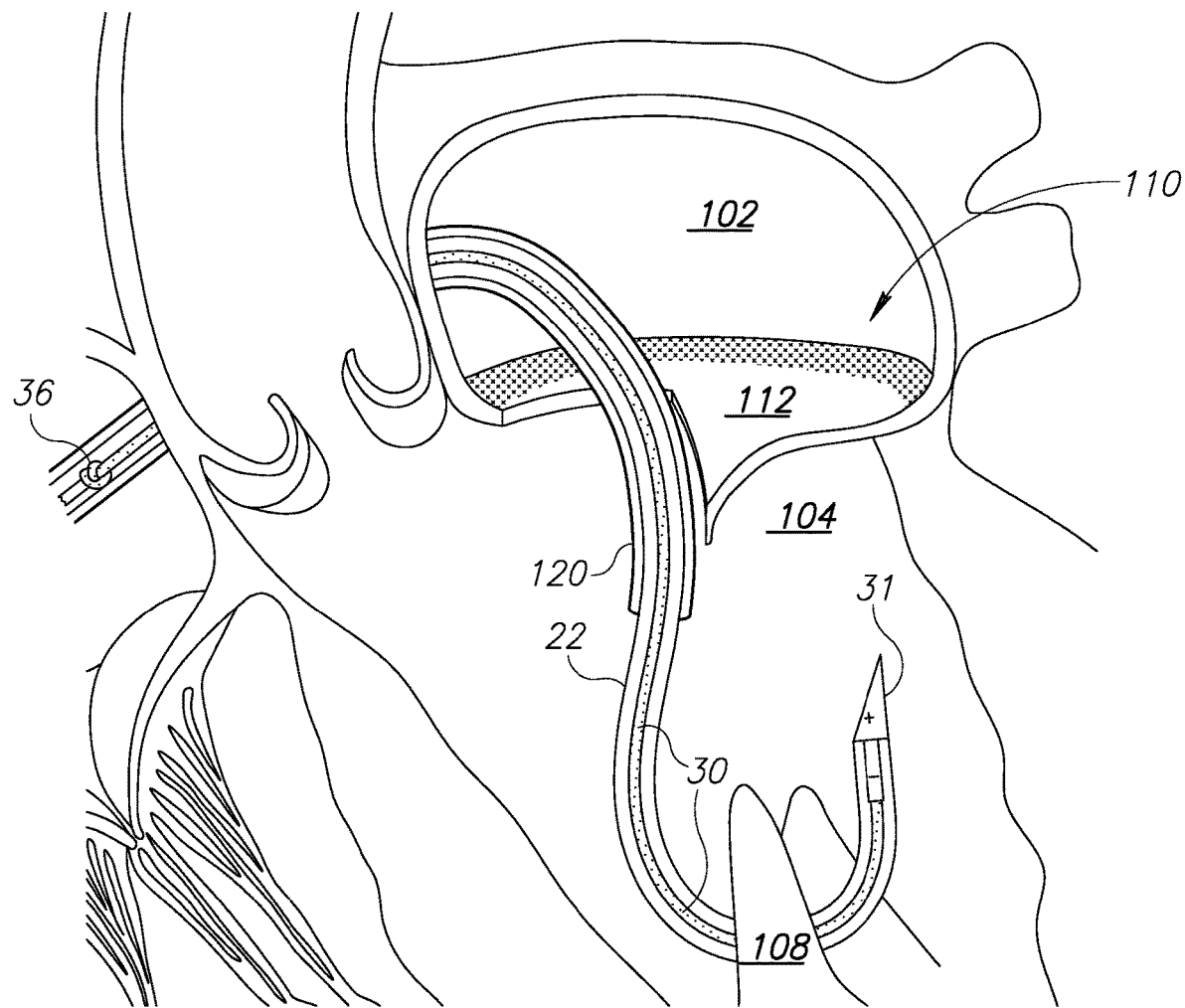
FIG. 7 schematically illustrates percutaneous deployment of a neochorda to a leaflet of a mitral valve via a transseptal approach, in accordance with an embodiment of the disclosure.

It is noted that whereas in the procedure schematically illustrated in FIGS. 6A-6L catheter 120 delivers neochorda delivery system 20 through the aortic valve 106, in an embodiment neochorda delivery system 20 may be introduced into the left ventricle in a transseptal approach. In the transseptal approach the neochorda delivery system 20 as well as clamping system 50 and retriever system 70 (FIGS. 6C-6H) are introduced into the left atrium via a puncture hole in the cardiac septum through a same puncture hole in the septum or different puncture holes in the septum. By way of example, FIG. 7 schematically shows a transseptal introduction of neochorda delivery system 20 into ventricle 104, in accordance with an embodiment. In FIG. 7 the neochorda delivery system is shown introduced into the ventricle between edges of anterior and posterior leaflets 112 and 114 in a transseptal approach after puncturing the cardiac septum.

It is further noted that whereas FIGS. 6A-6L and 7 schematically show a procedure in which neochorda delivery system 20 is introduced to ventricle 104 through aortic valve 106, or in a transseptal approach through a space between edges the mitral valve, practice of an embodiment of the disclosure is not limited to the delivery formats shown in the figures. Retriever system 70 may be introduced to ventricle 104 through the aortic valve 106 or through a puncture hole in a leaflet of the mitral valve.

There is therefore provided in accordance with an embodiment of the disclosure an apparatus for coupling a prosthetic chorda to an atrioventricular valve leaflet, the apparatus comprising: a neochorda delivery system comprising a steerable and pushable clamping catheter housing a neochorda attached to a neochorda puncture needle, the clamping catheter operable to push the puncture needle to puncture and thread the neochorda through a papillary muscle of a ventricle; a retriever system comprising a retriever catheter housing a grabber operable to capture the neochorda puncture needle after being threaded through the papillary muscle and withdraw the neochorda puncture needle and neochorda from the ventricle; and a tissue clamping system comprising a clamping catheter housing distal and proximal tissue clamps deployable to clamp a region of an atrioventricular valve between them and hold the region so that it may be punctured to thread the neochorda through the leaflet.

Optionally, the clamping catheter slidably houses the neochorda catheter. Alternatively, the clamping catheter slidably houses the retriever catheter.

In an embodiment the retriever catheter houses a gripping catheter having a distal end to which the set of gripping jaws are attached. Optionally, the retriever system comprises a capture needle for coupling to the puncture needle. The apparatus may comprise a pushable pull wire having a distal end to which the capture needle is attached. Optionally, the pushable pull wire is housed in the gripping catheter.

In an embodiment the puncture needle and capture needles are magnetized. The distal ends of the puncture and capture needles may have opposite magnetic polarity.

In an embodiment, the expanded shape the proximal clamp comprises a horseshoe shaped end for clamping a region of an atrioventricular valve. In an embodiment, the expanded shape the distal clamp comprises a horseshoe shaped end for clamping a region of an atrioventricular valve.

The apparatus may comprise a lock deployment system operable to lock the neochorda to the atrioventricular leaflet, and comprising: a first catheter having a lumen in which the neochorda is slidably received; a neochorda lock having an unlocked state in which state the lock grips the first catheter and is slidable along the neochorda, and a locked state in which the neochorda lock does not grip the first catheter and is locked to the neochorda and the atrioventricular leaflet; a second catheter housing the first catheter and the neochorda lock in the unlocked state with the lock pressing against and holding onto an inner surface of the second catheter; wherein the lock is releasable to lock to the neochorda and atrioventricular leaflet by sliding the first and second catheters relative to each other.

Optionally, the neochorda lock comprises a plurality of cable clamps and in the unlocked state the cable clamps grip the first catheter and in the locked state the cable clamps grip the neochorda. The neochorda lock optionally comprises a plurality of legs that extend out in directions substantially perpendicular to the first catheter to grip and lock the lock to tissue of the atrioventricular leaflet. Optionally, in the unlocked state the legs are folded back in a proximal direction to press against the inner surface of the second catheter, and in the locked state the cable clamps splay out to extend and lock the lock to the tissue of the atrioventricular leaflet. Optionally, the legs are formed having barbed ends that puncture the tissue of the atrioventricular leaflet to lock the lock to the tissue of the atrioventricular leaflet.

There is further provided in accordance with an embodiment a tissue clamping system comprising: a clamping catheter; a first tissue clamp comprising a first pushable stem wire extending along the clamping catheter and comprising a first clamping end held in a collapsed state inside the clamping catheter that assumes an expanded state when pushed out from the clamping catheter; and a second tissue clamp comprising a second pushable stem wire extending along the clamping catheter and comprising a second clamping end held in a collapsed state inside the clamping catheter that assumes an expanded state when pushed out from the clamping catheter; wherein, the first and second clamping ends are sequentially pushable out from the clamping catheter to clamp a region of a layer of tissue between them.

There is further provided in accordance with an embodiment apparatus for coupling a neochorda to an atrioventricular valve leaflet of a heart, the apparatus comprising: a tissue clamping system in accordance with an embodiment of the disclosure; a neochorda delivery system operable to puncture and thread a neochorda through a region of the leaflet clamped by the clamping system and thread the neochorda through a papillary muscle of a ventricle of the heart; and a retriever system operable to capture the neochorda puncture needle after the puncture needle has punctured and threaded the neochorda through the papillary muscle. Optionally, the neochorda delivery system or the retriever system is housed in the clamping catheter.

There is further provided in accordance with an embodiment a lock deployment system operable to lock a fiber to a region of tissue the system comprising: a first catheter having a lumen in which the fiber is slidably received; a fiber lock having an unlocked state in which state the lock grips the first catheter and is slidable along the fiber, and a locked state in which the fiber lock does not grip the first catheter and is locked to the fiber and the region of tissue; a second catheter housing the first catheter and the fiber lock in the unlocked state with the lock pressing against and holding onto an inner surface of the second catheter; wherein the lock is releasable to lock to the fiber and the region of tissue by sliding the first and second catheters relative to each other.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims as follows.

The invention claimed is:

1. An apparatus for coupling a prosthetic chorda to an atrioventricular valve leaflet, the apparatus comprising:
   a neochorda delivery system comprising a steerable and pushable neochorda catheter housing a neochorda attached to a neochorda puncture needle, the neochorda catheter operable to push the puncture needle to puncture and thread the neochorda through a papillary muscle of a ventricle;
   a retriever system comprising a retriever catheter housing a grabber operable to capture the neochorda puncture needle after being threaded through the papillary muscle and withdraw the neochorda puncture needle and neochorda from the ventricle; and a tissue clamping system comprising a clamping catheter housing distal and proximal tissue clamps deployable to clamp a region of an atrioventricular valve between them and hold the region so that it may be punctured to thread the neochorda through the leaflet.

2. The apparatus according to claim 1, wherein the clamping catheter slidably houses the neochorda catheter.

3. The apparatus according to claim 1, wherein the clamping catheter slidably houses the retriever catheter.

4. The apparatus according to wherein the retriever catheter houses a gripping catheter having a distal end that comprises the grabber to which set of gripping jaws are attached.

5. The apparatus according to claim 4, wherein the retriever system comprises a capture needle for coupling to the puncture needle.

6. The apparatus according to claim 5, comprising a pushable pull wire having a distal end to which the capture needle is attached.

7. The apparatus according to claim 6, wherein the pushable pull wire is housed in the gripping catheter.

8. The apparatus according to claim 5 wherein the puncture needle and capture needles are magnetized.

9. The apparatus according to claim 8, wherein distal ends of the puncture needle and the capture needles have opposite magnetic polarity.

10. The apparatus according to claim 1 wherein in an expanded shape the proximal clamp comprises a horseshoe shaped end for clamping a region of an atrioventricular valve.

11. The apparatus according to claim 1 wherein in an expanded shape the distal clamp comprises a horseshoe shaped end for clamping a region of an atrioventricular valve.

12. The apparatus according to claim 1, comprising a lock deployment system operable to lock the neochorda to the atrioventricular leaflet, and comprising:

a first catheter having a lumen in which the neochorda is slidably received;

a neochorda lock having an unlocked state in which state the lock grips the first catheter and is slidable along the neochorda, and a locked state in which the neochorda lock does not grip the first catheter and is locked to the neochorda and the atrioventricular leaflet;

a second catheter housing the first catheter and the neochorda lock in the unlocked state with the lock pressing against and holding onto an inner surface of the second catheter;

wherein the lock is releasable to lock to the neochorda and atrioventricular leaflet by sliding the first and second catheters relative to each other.

13. The apparatus according to claim 12, wherein the neochorda lock comprises a plurality of cable clamps and in the unlocked state the cable clamps grip the first catheter and in the locked state the cable clamps grip the neochorda.

14. The apparatus according to claim 13, wherein the neochorda lock comprises a plurality of legs that extend out in directions substantially perpendicular to the first catheter to grip and lock the lock to tissue of the atrioventricular leaflet.

15. The apparatus according to claim 14, wherein in the unlocked state the legs are folded back in a proximal direction to press against the inner surface of the second catheter, and in the locked state the cable clamps splay out to extend and lock the lock to the tissue of the atrioventricular leaflet.

16. The apparatus according to claim 15, wherein the legs are formed having barbed ends that puncture the tissue of the atrioventricular leaflet to lock the lock to the tissue of the atrioventricular leaflet.

* * * * *